(12) United States Patent
Levings et al.

(10) Patent No.: US 11,367,023 B2
(45) Date of Patent: Jun. 21, 2022

(54) PATIENT MANAGEMENT SYSTEM

(71) Applicant: ResMed Inc., San Diego, CA (US)

(72) Inventors: Robert Andrew Levings, Halifax (CA); Ryan Eric Belbin, Hammonds Plains (CA); Mark David Buckley, Sydney (AU); Michael Waclaw Colefax, Sydney (AU); Jason Connell, Lucasville (CA); Cheryl Kazimer, Beechville (CA); Colin Bradley Kennedy, Nova Scotia (CA); Susan Robyn Lynch, Maitland (AU); Rehana Nathwani, Sydney (AU); Timothy Semen, Ambler, PA (US); Rajwant Sodhi, Halifax (CA)

(73) Assignee: ResMed Inc., San Diego, CA (US)

( * ) Notice: Subject to any disclaimer, the term of this patent is extended or adjusted under 35 U.S.C. 154(b) by 82 days.

(21) Appl. No.: 15/329,853

(22) PCT Filed: Jul. 31, 2015

(86) PCT No.: PCT/US2015/043226
§ 371 (c)(1),
(2) Date: Jan. 27, 2017

(87) PCT Pub. No.: WO2016/019304
PCT Pub. Date: Feb. 4, 2016

(65) Prior Publication Data
US 2017/0186122 A1    Jun. 29, 2017

Related U.S. Application Data

(60) Provisional application No. 62/072,107, filed on Oct. 29, 2014, provisional application No. 62/031,975, filed on Aug. 1, 2014.

(51) Int. Cl.
*G06Q 10/00* (2012.01)
*G16H 20/40* (2018.01)
(Continued)

(52) U.S. Cl.
CPC ......... *G06Q 10/00* (2013.01); *A61M 16/0633* (2014.02); *A61M 16/0666* (2013.01);
(Continued)

(58) Field of Classification Search
CPC ........ G16H 10/00; G16H 10/20; G16H 15/00; G16H 20/00; G16H 20/30; G16H 20/70;
(Continued)

(56) References Cited

U.S. PATENT DOCUMENTS 4,944,310 A    7/1990  Sullivan
5,931,160 A    8/1999  Gilmore et al.
(Continued)

FOREIGN PATENT DOCUMENTS

JP    2009039357 A    8/2007
JP    2010509659 A    3/2010
(Continued)

OTHER PUBLICATIONS

Valentin et al., Air Leak Is Associated With Poor Adherence to AutoPAP Therapy, SLEEP, vol. 34, No. 6, 2011, pp. 801-806 (Year: 2011).*

(Continued)

*Primary Examiner* — Jason S Tiedeman
(74) *Attorney, Agent, or Firm* — Botos Churchill IP Law LLP

(57) ABSTRACT

Methods and Systems implement patient management. In some cases, a patient management system 200 may include one or more respiratory pressure therapy devices to deliver respiratory pressure therapy to patients, and generate therapy data relating to a therapy session for a patient. The
(Continued)

patient management system may include a data server communicating with the therapy device(s). The data server may compute, from therapy data, therapy summary data for the session, the summary data may include one or more statistics summarising therapy data. The patient management system may include a therapy management server communicating with the data server. The therapy management server may apply one or more rules to the summary data, update or generate one or more workflow groups of patients, each workflow group corresponding to a rule, depending on results of the respective rule applications; and/or serve a graphical layout representing one or more workflow groups.

30 Claims, 13 Drawing Sheets

(51) Int. Cl.
*G16H 40/67* (2018.01)
*A61M 16/06* (2006.01)
*A61M 5/00* (2006.01)
*A61M 16/00* (2006.01)
*G06Q 50/20* (2012.01)

(52) U.S. Cl.
CPC ........ *A61M 16/0683* (2013.01); *G16H 20/40* (2018.01); *G16H 40/67* (2018.01); *A61M 5/00* (2013.01); *A61M 16/06* (2013.01); *A61M 2016/003* (2013.01); *A61M 2016/0027* (2013.01); *A61M 2202/0208* (2013.01); *A61M 2205/3584* (2013.01); *A61M 2205/502* (2013.01); *G06Q 50/20* (2013.01); *Y02A 90/10* (2018.01)

(58) Field of Classification Search
CPC ........ G16H 40/00; G16H 40/60; G16H 40/63; G16H 20/40; G16H 40/67; G06Q 50/22; G06Q 50/24; G06Q 50/20; G06Q 10/00; G06F 19/30; G06F 19/32; G06F 19/34; G06F 19/3456; G06F 19/3481; G06F 19/36; G06F 19/325; A61M 16/06; A61M 16/0633; A61M 16/0683; A61M 5/00; A61M 2016/0027; A61M 2016/003; A61M 2202/0208; A61M 2205/3584; A61M 2205/502; Y02A 90/10
USPC ....................................................... 705/2, 3
See application file for complete search history.

(56) References Cited

U.S. PATENT DOCUMENTS

| | | | |
|---|---|---|---|
| 6,039,688 A | 3/2000 | Douglas et al. | |
| 6,299,581 B1 | 10/2001 | Rapoport et al. | |
| 6,532,959 B1 | 3/2003 | Berthon-Jones | |
| 7,866,944 B2 | 1/2011 | Kenyon et al. | |
| 8,528,551 B2 | 9/2013 | Mulcahy et al. | |
| 8,636,479 B2 | 1/2014 | Kenyon et al. | |
| 8,638,014 B2 | 1/2014 | Sears et al. | |
| 8,666,926 B1* | 3/2014 | Nease | G06N 5/022 706/50 |
| 8,775,200 B1* | 7/2014 | Dunn | G06Q 50/22 705/2 |
| 2002/0007284 A1* | 1/2002 | Schurenberg | G06Q 10/10 705/2 |
| 2003/0208465 A1 | 11/2003 | Yurko et al. | |
| 2003/0212579 A1* | 11/2003 | Brown | A61B 5/411 600/300 |
| 2003/0217111 A1* | 11/2003 | McKay | G16Z 99/00 707/E17.116 |
| 2003/0236450 A1 | 12/2003 | Kocinski | |
| 2006/0130836 A1 | 6/2006 | Wixey et al. | |
| 2006/0276727 A1* | 12/2006 | Terrio | G16H 10/20 600/595 |
| 2007/0016440 A1* | 1/2007 | Stroup | G16H 10/40 705/2 |
| 2007/0022086 A1* | 1/2007 | Elsholz | G16H 40/63 |
| 2008/0059224 A1 | 3/2008 | Schechter | |
| 2008/0114689 A1* | 5/2008 | Psynik | G06F 19/3418 705/51 |
| 2008/0140454 A1* | 6/2008 | Hernandez | G16H 30/20 705/3 |
| 2008/0140723 A1* | 6/2008 | Hernandez | G16H 30/20 |
| 2009/0125328 A1 | 5/2009 | Nevins | |
| 2010/0017231 A1* | 1/2010 | Galbraith | G16H 50/20 715/764 |
| 2010/0049008 A1 | 2/2010 | Doherty et al. | |
| 2010/0138232 A1* | 6/2010 | Ryan | G16H 40/67 705/2 |
| 2010/0170513 A1 | 7/2010 | Bowditch et al. | |
| 2010/0305966 A1* | 12/2010 | Coulter | G06Q 10/06 705/2 |
| 2011/0077970 A1* | 3/2011 | Mellin | G16H 40/67 705/3 |
| 2011/0112857 A1 | 5/2011 | Yurko et al. | |
| 2011/0166884 A1* | 7/2011 | Lesselroth | G16H 10/60 705/3 |
| 2011/0178819 A1* | 7/2011 | Mchorney | G16H 10/20 705/2 |
| 2011/0192400 A9 | 8/2011 | Burton et al. | |
| 2011/0199214 A1 | 8/2011 | Gawlick | |
| 2011/0270623 A1* | 11/2011 | Reiner | G06F 19/321 705/2 |
| 2011/0295083 A1 | 12/2011 | Doelling et al. | |
| 2012/0072238 A1 | 3/2012 | Collins, Jr. et al. | |
| 2012/0215081 A1 | 8/2012 | Euliano et al. | |
| 2012/0240933 A1 | 9/2012 | Haas | |
| 2012/0265552 A1* | 10/2012 | Rabinowitz | G16H 10/60 705/2 |
| 2013/0110545 A1* | 5/2013 | Smallwood | G16H 10/60 705/3 |
| 2013/0317765 A1* | 11/2013 | Rao | A61M 16/0051 702/51 |
| 2013/0317839 A1* | 11/2013 | Creswell | G16H 10/60 705/2 |
| 2013/0317840 A1* | 11/2013 | Creswell | G16H 20/10 705/2 |
| 2014/0019162 A1* | 1/2014 | Skowronski | G16H 10/60 705/3 |
| 2014/0048072 A1 | 2/2014 | Angelico et al. | |
| 2014/0155705 A1* | 6/2014 | Papadopoulos | A61B 5/0004 600/301 |
| 2014/0278679 A1* | 9/2014 | Navani | G06Q 10/06311 705/7.19 |
| 2015/0100327 A1* | 4/2015 | Kelly | G16H 10/60 705/2 |
| 2015/0112700 A1* | 4/2015 | Sublett | G16H 40/20 705/2 |
| 2015/0154380 A1* | 6/2015 | Duckworth | G06F 19/3481 705/2 |
| 2015/0174347 A1 | 6/2015 | Kirby et al. | |
| 2015/0186602 A1* | 7/2015 | Pipke | A61B 5/743 705/3 |
| 2016/0019351 A1* | 1/2016 | Ober, Jr. | G06F 40/295 705/3 |

FOREIGN PATENT DOCUMENTS

| | | | |
|---|---|---|---|
| JP | 2010514497 A | 5/2010 | |
| JP | 2015529359 A | 10/2015 | |
| WO | 2008085308 A1 | 7/2008 | |
| WO | WO-2010104978 A2 * | 9/2010 | ........ A61B 5/4833 |
| WO | 2013020167 A1 | 2/2013 | |
| WO | 2013033419 A1 | 3/2013 | |
| WO | 2013187776 A1 | 12/2013 | |

(56) References Cited

FOREIGN PATENT DOCUMENTS

| WO | 2014013411 A1 | 1/2014 |
| WO | 2014028888 A3 | 4/2014 |
| WO | 2008057952 A2 | 5/2019 |

OTHER PUBLICATIONS

Extended European Search Report and Written Opinion in EP15828142 dated Mar. 1, 2018.
Extended European Search Report and Written Opinion for EP15827493.6 dated Apr. 13, 2018.
ResTraxx System User Guide, ResMed Limited, Jan. 2, 2008. Retrieved from the Internet: http://manualzz.com/doc/7495030/restraxx%E2%84%A2-system--apria-healthcare [retrieved Mar. 29, 2018].
Stepnowsky Jr. et al., "Pilot Randomized Trial of the Effect of Wireless Telemonitoring on Compliance and Treatment Efficacy in Obstructive Sleep Apnea," Jouml of Medical Internet Research, Apr.-Jun. 2007, vol. 9(4), pp. 1-22 (published onl;ine May 17, 2007).
Stepnowsky CJ, Marler MR, Ancoli-Israel S. Determinants of nasal CPAP compliance. Sleep medicine. May 1, 2002;3(3):239-47.
International Search Report and Written Opinion for Application No. PCT/US2015/043204 dated Oct. 26, 2015.
International Search Report and Written Opinion for Application No. PCT/US2015/043226 dated Dec. 30, 2015.
John B. West, Respiratory Physiology: The Essentials, Lippincott Williams & Wilkins, 9th Edition, published Sep. 21, 2011.
EP Communication dated Apr. 7, 2020, EP Application No. 15827493.6.
JP Office Action dated Sep. 1, 2020, EP Patent Application No. P2017-505512.
Ghosh, Dipansu, et al., "Identifying poor compliance with CPAP in obstructive sleep apnoea: A simple prediction equation using data after a two week trial", Respiratory Medicine 107, 936-942, 2013.

\* cited by examiner

PATIENT MANAGEMENT SYSTEM

CROSS-REFERENCE TO RELATED APPLICATIONS

The present application is a national phase entry under 35 U.S.C. § 371 of International Application No. PCT/US2015/043226 filed Jul. 31, 2015, published in English, which claims priority from U.S. Provisional Patent Application No. 62/072,107 filed Oct. 29, 2014 and U.S. Provisional Patent Application No. 62/031,975 filed Aug. 1, 2014 all of which are incorporated herein by reference.

STATEMENT REGARDING FEDERALLY SPONSORED RESEARCH OR DEVELOPMENT

Not Applicable

THE NAMES OF PARTIES TO A JOINT RESEARCH DEVELOPMENT

Not Applicable

SEQUENCE LISTING

Not Applicable

BACKGROUND OF THE TECHNOLOGY

Field of the Technology

The present technology relates to one or more of the detection, diagnosis, treatment, prevention and amelioration of respiratory-related disorders. The present technology also relates to medical devices or apparatus, and their use.

Description of the Related Art

Human Respiratory System and its Disorders

The respiratory system of the body facilitates gas exchange.

The nose and mouth form the entrance to the airways of a patient. The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2011.

A range of respiratory disorders exist. Certain disorders may be characterised by particular events, e.g. apneas, hypopneas, and hyperpneas.

Obstructive Sleep Apnea (OSA), a form of Sleep Disordered Breathing (SDB), is characterized by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

A range of therapies have been used to treat or ameliorate such conditions. Furthermore, otherwise healthy individuals may take advantage of such therapies to prevent respiratory disorders from arising. However, these have a number of shortcomings.

Respiratory Pressure Therapies

In some forms of respiratory pressure therapy, the treatment pressure Pt is held close to a base pressure $P_0$ throughout the patient's respiratory cycle. Such forms are generally referred to as Continuous Positive Airway Pressure (CPAP) therapy. CPAP therapy has been used to treat OSA. The mechanism of action is that continuous positive airway pressure acts as a pneumatic splint and may prevent upper airway occlusion by pushing the soft palate and tongue forward and away from the posterior oropharyngeal wall. In one implementation of CPAP therapy, sometimes referred to as constant CPAP therapy, the base pressure $P_0$ may be a constant value that is prescribed or determined during titration. Alternatively, the base pressure $P_0$ may be dynamically computed as a function of indices or measures of sleep disordered breathing, such as one or more of flow limitation, apnea, hypopnea, airway patency, and snore. This implementation is sometimes referred to as APAP therapy.

Treatment of OSA by CPAP therapy may be voluntary, and hence patients may elect not to comply with therapy if they find devices used to provide such therapy one or more of: uncomfortable, difficult to use, expensive and aesthetically unappealing.

In another form of respiratory pressure therapy, the treatment pressure Pt oscillates in synchronisation with the patient's respiratory cycle to assist the patient in taking a full breath and/or to maintain adequate oxygen levels in the body by doing some or all of the work of breathing of the patient. Such forms are known as pressure support ventilation therapy, and may be used to treat CSR or COPD.

Treatment Systems

Respiratory pressure therapies may be provided by a treatment system or device. A treatment system may comprise a respiratory pressure therapy device (RPT device), an air circuit, a humidifier, a patient interface, and data management.

Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O.

Respiratory Pressure Therapy (RPT) Device

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air. A range of artificial humidification devices and systems are known, however they may not fulfil the specialised requirements of a medical humidifier.

Data Management

Insurance companies, or other reimbursing entities (payors), often require evidence that a patient prescribed with respiratory pressure therapy has been "compliant", that is, used their RPT device according to certain a "compliance standard" before reimbursing the patient for the RPT device. Compliance standards generally require some minimum amount of usage per session for some fraction of a number of consecutive sessions known as the compliance period. One example of a compliance standard for CPAP therapy common to many payors, known as the CMS compliance standard, is that a patient is required to use the RPT device for at least four hours a night on at least 21 of 30 consecutive days. In order to determine a patient's compliance, a provider of the RPT device (such as a durable medical equipment provider or DME, also sometimes referred to as a home medical equipment provider or HME) may manually obtain data describing the patient's therapy using the RPT device, calculate the device usage from the therapy data, and compare the usage with the compliance standard. Once the DME has determined that the patient is compliant according to the compliance standard, the DME may notify the reimbursing entity that the patient is compliant. This process can be costly, time-consuming, and error-prone if conducted manually. RPT devices typically therefore contain data management capability that enables the RPT device to store and transmit therapy data to a remote server to determine automatically whether the patient has used the RPT device in accordance with the compliance standard.

Compliance Problems

Studies have shown that up to 90% of patients prescribed with CPAP therapy (CPAP patients) have at least some problems meeting compliance standards. Difficulty in setting up an RPT device, discomfort due to an ill-fitting or ill-adjusted patient interface, lack of tolerance for the sensation of positive airway pressure at the prescribed level, excessive leaks causing noise or disruption to the patient or their bed partner, and lack of improvement in subjective well-being are all examples of such problems. Many patients simply give up after early difficulties, some of which would be readily overcome by a simple contact by the patient's DME to ascertain the difficulty and take or recommend corrective action. Many CPAP patients are therefore missing out on beneficial therapy for reasons that are avoidable if their DME had access to timely information about the progress of their therapy and any difficulties they are experiencing. The data management capability of RPT devices described above may enable such access by DMEs. However, if simply presented with raw therapy data from the potentially large number of CPAP patients under their care, an agent of a DME may have no idea which patients have compliance issues and which do not.

A need therefore exists to provide DMEs with information about the progress of their CPAP patients' therapy, in such a way that patients experiencing, or at risk of experiencing, compliance difficulties are prominently featured.

BRIEF SUMMARY OF THE TECHNOLOGY

The present technology is directed towards the management of therapy for the amelioration, treatment, or prevention of respiratory disorders.

A first aspect of the present technology relates to a patient management system that improves the compliance of patients with respiratory pressure therapy.

One form of the present technology includes a patient management system that displays therapy summary data to an agent of a patient's DME in a manner that emphasises where potential therapy problems lie and thus where attention is most needed. A set of rules are applied to the therapy summary data, the results of each rule defining a workflow group of patients satisfying the rule and therefore requiring attention. The agent may view a display of all the workflow groups. The agent may activate a group to display the group members and review their status before taking the action specified by the workflow, upon which they may be manually removed from the workflow group. The agent may also view a history of the workflow group addition/removal of each patient.

In accordance with one aspect of the present technology, there is provided a patient management system. The patient management system may include a data server in communication with a plurality of respiratory pressure therapy devices. The respiratory pressure therapy devices may each be configured to deliver respiratory pressure therapy to a patient, and to generate therapy data relating to a session of respiratory pressure therapy. The data server may be configured to compute, from the therapy data, therapy summary data for the session. The therapy summary data may include one or more statistics summarising the therapy data. The system may include a therapy management server in communication with the data server. The therapy management server may be configured to apply one or more rules to the therapy summary data. The therapy management server may be configured to update one or more workflow groups of patients (e.g., a plurality of workflow groups), each workflow group corresponding to a rule, depending on results of the respective rule applications. The therapy management server may be configured to serve a graphical layout representing the one or more workflow groups.

In accordance with a second aspect of the present technology, there is provided a patient management system. The patient management system may include a therapy management server in communication with a respiratory pressure therapy device, wherein the respiratory pressure therapy device may be configured to deliver respiratory pressure therapy to a patient during a session and to compute, from therapy data relating to a session of respiratory pressure therapy, therapy summary data for the session. The therapy summary data may include one or more statistics summarising the therapy data. The therapy management server may be configured to apply one or more rules to the therapy summary data. The therapy management server may be configured to update one or more workflow groups (e.g., a plurality of workflow groups), each workflow group corresponding to a rule, depending on results of the respective rule applications. The therapy management server may be configured to serve a graphical layout representing the one or more workflow groups.

In accordance with a third aspect of the present technology, there is provided a method of managing one or more patients undergoing respiratory pressure therapy. The method may include applying, by a therapy management server, one or more rules to therapy summary data that may include one or more statistics summarising therapy data relating to a session of respiratory pressure therapy for a patient. The method may include updating, by the therapy management server, one or more workflow groups (e.g., a plurality of workflow groups), each workflow group corresponding to a rule, depending on results of the respective rule applications. The method may include serving, by the therapy management server, a graphical layout representing the one or more workflow groups.

In accordance with a fourth aspect of the present technology, there is provided a respiratory pressure therapy management server. The respiratory pressure therapy management server may be configured to apply one or more rules to therapy summary data including one or more statistics summarising therapy data relating to a session of respiratory pressure therapy for a patient. The respiratory pressure therapy management server may be configured to update one or more workflow groups, each workflow group corresponding to a rule, depending on results of the respective rule applications. The respiratory pressure therapy management server may be configured to serve a graphical layout representing the one or more workflow groups.

Other aspects of the present technology may be considered in reference to the particular examples and claims recited herein.

Systems and methods described herein provide technological solutions to help improve patient therapy and/or compliance with therapy such as when using a therapy device (e.g., a respiratory pressure therapy device). Moreover, in some cases it may assist with the management of such patients by a management entity (e.g., clinicians/caregivers, etc.). Moreover, the methods and systems provide improvements in the functioning of processors such as for, or control of, therapy devices and/or management or monitoring computer systems (e.g., servers).

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

BRIEF DESCRIPTION OF THE DRAWINGS

The present technology is illustrated by way of example, and not by way of limitation, in the figures of the accompanying drawings, in which like reference numerals refer to similar elements including:
Treatment Systems
FIGS. 4 to 13 are examples of graphical layouts served by the therapy management server in the patient management system of FIG. 2.

DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

Patient Management System

Figure 1:
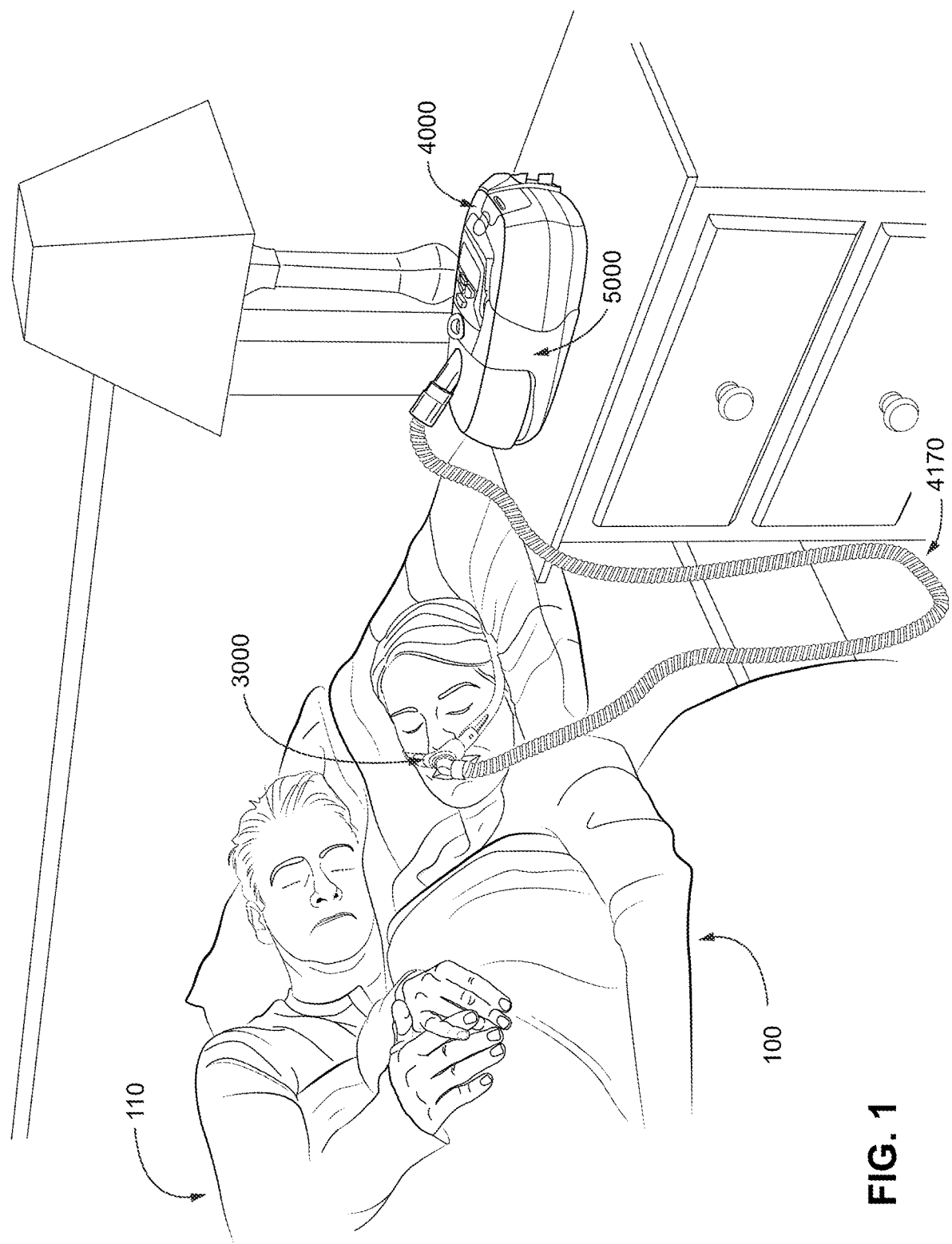
FIG. 1 is an illustration of a patient receiving respiratory pressure therapy.
Patient Management

FIG. 1 shows a system including a patient 100 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 100. A bed partner 110 is also shown.

Figure 2:
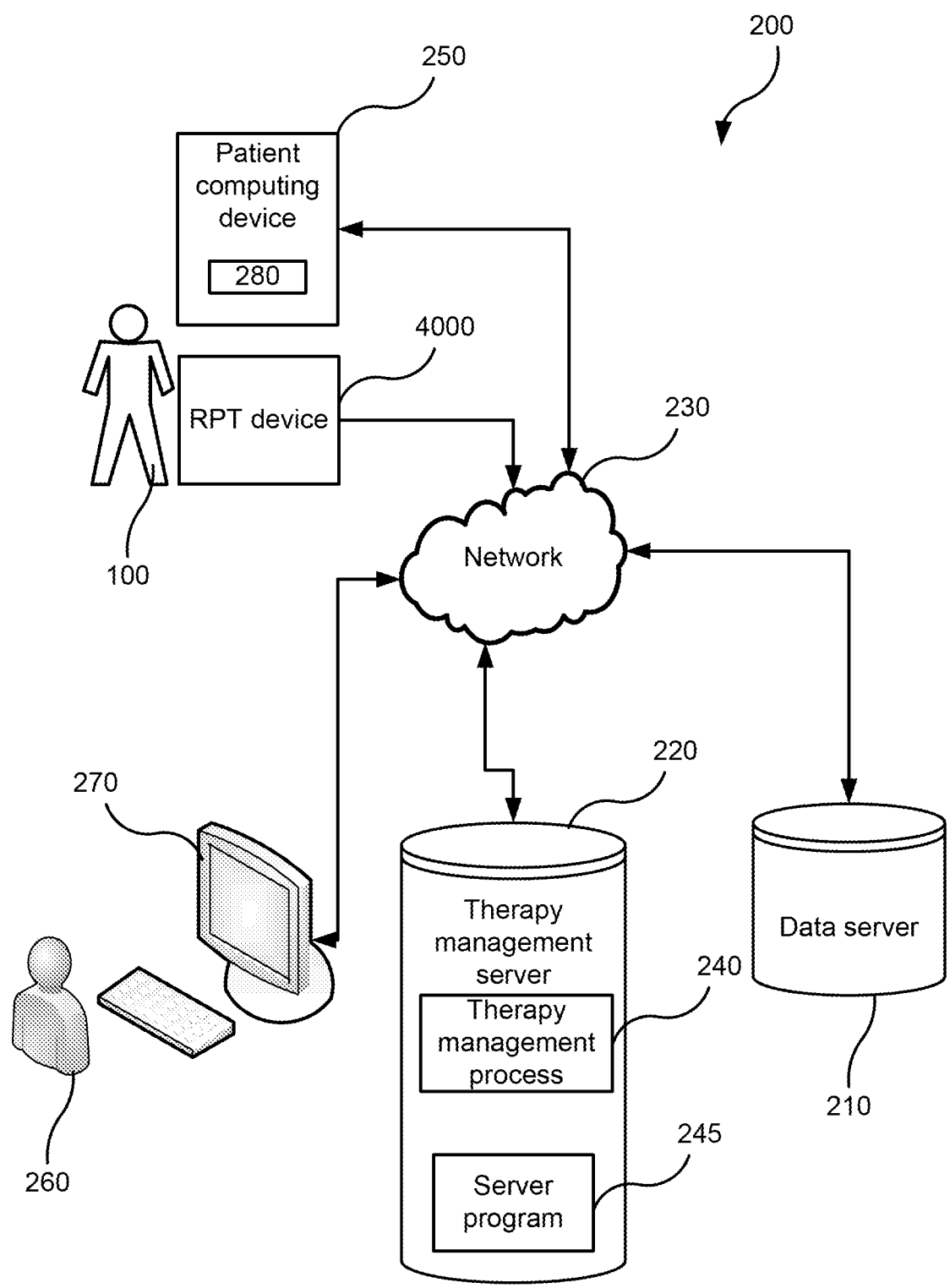
FIG. 2 is a block diagram of a patient management system according to one form of the present technology.

FIG. 2 is a block diagram of a patient management system 200 in one form of the present technology. The patient management system 200 comprises an RPT device 4000 configured to deliver respiratory pressure therapy to the patient 100 in the form of pressurised air to an entrance to the airway of the patient 100 during a therapy session. The RPT device 4000 is configured to transmit data concerning the therapy delivered to the patient 100 to a data server 210 via a network 230. The therapy data may comprise settings of the RPT device 4000, and/or data describing one or more of the variables of the therapy, e.g. flow rate, treatment pressure, and leak flow rate, over the therapy session.

The data server 210 is configured to receive the therapy data from the RPT device 4000 and to compute therapy summary data for the therapy session from the therapy data. The therapy summary data comprises one or more statistics summarising the therapy data, such as an Apnea/Hypopnea Index (AHI), or an average leak flow rate. Another example of a summary statistic is the number of hours for which the RPT device 4000 was used during the therapy session (this statistic is referred to as "usage time" or "usage data"). The data server 210 may use conventional scoring methods to generate the therapy summary data from the therapy data.

The data server 210 is configured to transmit, via the network 230, the therapy summary data to a therapy management server 220. The therapy management server 220 is configured to execute a therapy management process 240 that is described in more detail below with reference to FIG. 3, and a therapy management server program 245 that is described in more detail below with reference to FIGS. 4 to 13.

In an alternative implementation, the RPT device 4000 scores the therapy data and transmits the resulting therapy summary data to the data server 210, or directly to the therapy management server 220.

Also connected to the network 230 is a computing device 270 that is associated with an agent 260 of the DME that is responsible for the therapy of the patient 100. The agent 260 may be an employee of the DME such as a manager or a health care professional, or otherwise allied with the DME such as a contractor. The agent 260 interacts with the therapy management server 220 over the network 230 via a client program running on the computing device 270. The computing device 270 may be a desktop or portable (laptop or notebook) computer, tablet computer, or smartphone.

In an alternative configuration of the patient management system 200, the therapy management server 220 may be co-located and/or coincident with the data server 210. For example, multiple server apparatus may reside in a common data center and/or multiple server applications may reside on a common server apparatus.

The patient management system 200 may also contain a patient computing device 250, associated with the patient, connected to the network 230. The patient computing device 250 may be a personal computer, mobile phone, tablet computer, or other device. The patient computing device 250 is configured to intermediate between the patient 100 and the remotely located entities of the patient management system 200, principally the therapy management server 220, over the network 230. In the implementation of FIG. 2, this intermediation is accomplished by a patient program 280 that runs on the patient computing device 250. The patient program 280 may be referred to as a "patient app".

In an alternative implementation of the patient management system (not shown), the RPT device 4000 is not connected to the network 230, but is configured to communicate with the patient computing device 250 via a local wired or wireless network (not shown) based on a protocol such as Bluetooth or WiFi. In this alternative implementation, the patient computing device 250, via the patient app 280, intermediates between the RPT device 4000 and the remotely located entities of the patient management system over the network 230.

The patient management system 200 typically contains more than one patient, each with an associated RPT device and patient computing device, and more than one DME agent, each responsible for the therapy of one or more patients.

Therapy Management Process

Figure 3:
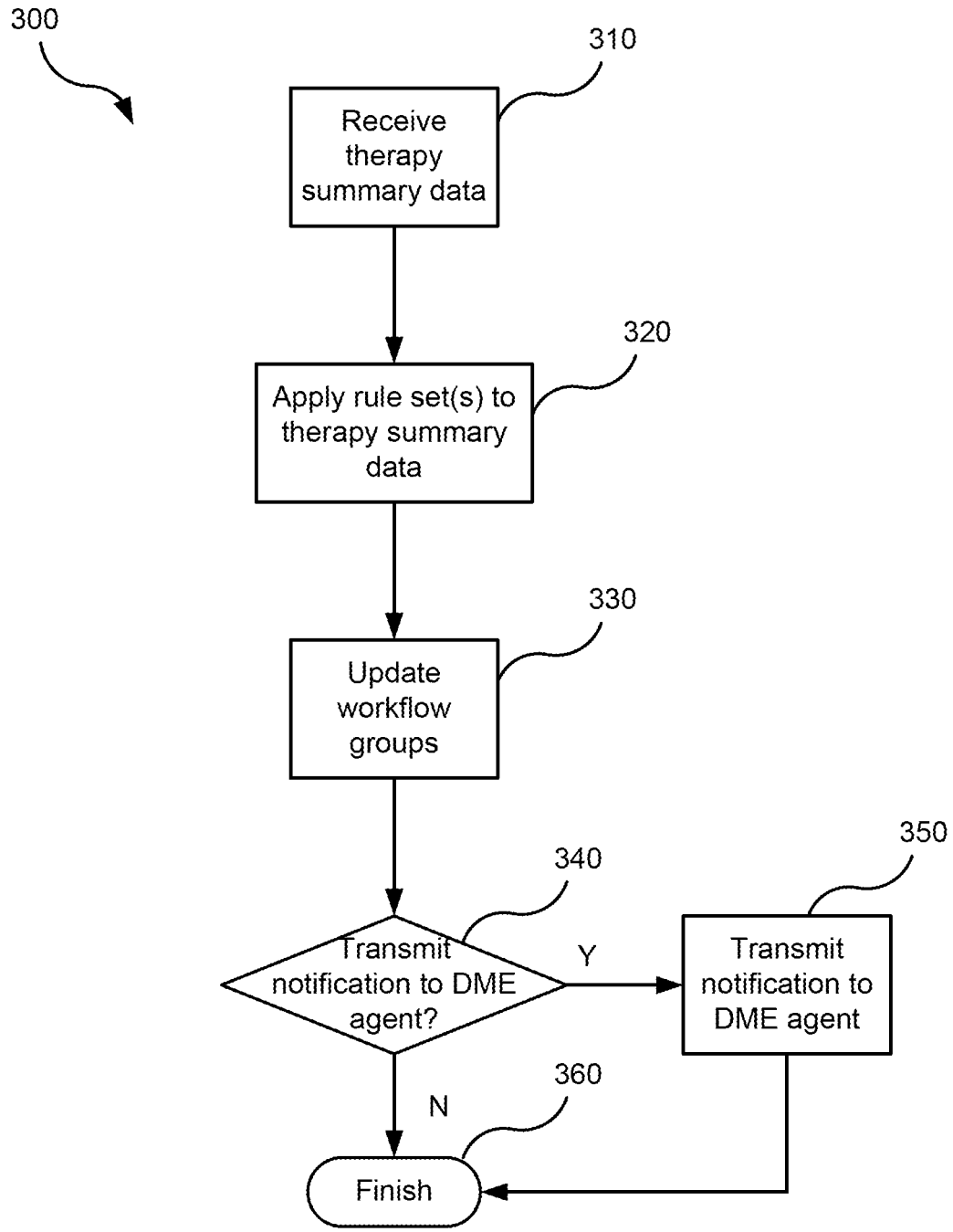
FIG. 3 is a flow chart illustrating a method that may be used as one implementation of a therapy management process carried out by the therapy management server of the patient management system of FIG. 2.

FIG. 3 is a flow chart illustrating a method 300 that may be used as one implementation of the therapy management process 240 carried out by the therapy management server 220 in the patient management system 200 of FIG. 2. The method 300 may be carried out each time the therapy management server 220 receives therapy summary data from the data server 210 or the RPT device 4000, or on a regular schedule such as each day.

The method 300 starts at step 310, at which the therapy management server 220 receives therapy summary data corresponding to one or more patients from the data server 210 or the RPT device 4000. At the next step 320, the therapy management server 220 applies one or more rule sets to the therapy summary data received at step 310 and (possibly) previously received therapy summary data. Step 330 follows, at which the therapy management server 220 updates one or more "workflow groups" based on the results of the rule applications at step 320. The results for each rule comprise a set of zero or more patients that satisfy the rule. Each rule defines a group of patients that satisfy the rule. The groups are termed "workflow groups" because some action specified by a workflow needs to be taken for each patient that satisfies a rule. An action may be a manual action taken by the DME agent 260, for example. One example of such a manual action is contacting the patient, e.g. by telephone (termed an "engagement"). Actions may also be "automated" i.e. automatically performed, for example, by the therapy management server 220. Automatic actions may include, for example, sending an email or text message to a patient that satisfies a rule. The updating at step 330 involves adding any patient whose therapy summary data satisfies a rule to the associated workflow group if they are not already in the workflow group. Step 330 involves updating a therapy management database that stores details of the workflow groups.

Each rule in a rule set comprises a condition that is applicable to one or more features of the therapy summary data. A rule is satisfied if the one or more features of the therapy summary data satisfy the condition comprised by the rule. Each rule in a rule set falls into one of multiple categories depending on the nature of the condition associated with the rule. In some implementations, the categories may include clinical, compliance, time-based, and "at risk". An example of a clinical condition is "Apnea/Hypopnea Index for a therapy session is greater than 10", or "Average leak flow rate for a therapy session is above 20 litres/minute". An example of a compliance condition is "Usage does not comply with predetermined compliance standard". The predetermined compliance standard may be a payor compliance standard such as CMS, or a compliance standard configured especially for the DME. An example of a time-based condition is "Patient has been on therapy for 7 days". Time-based rules do not require any therapy summary data and so are applied to all the patients undergoing respiratory pressure therapy being managed by the DME.

In some implementations, the action specified by a workflow associated with a rule may include more detail about the content of the action. For example, for the clinical rule whose condition is "Average leak flow rate for a therapy session is above 20 litres/minute", the specified action may be to manually contact the patient to discuss how to improve the fit of their patient interface 3000. As another example, for a compliance rule whose condition is "Patient is compliant after 90 days", the specified action may be to compile a compliance report for the payor associated with the patient.

"At risk" rules attempt to identify patients that are at risk of not being compliant with a predetermined compliance standard before they have reached the compliance period. Conditions associated with "at risk" rules utilise a Success Predictor Score (SPS), which indicates a probability that the patient 100 will meet the compliance standard. In one example, the SPS is a numerical value, such as a percentage or fraction representing the probability that the patient will be compliant. Alternatively, the SPS may be one of a set of labels indicating the likelihood of future compliance, such as: 'very unlikely', 'unlikely', 'moderately likely', 'likely', and 'very likely'.

In some implementations of the patient management system 200, the data server 210 or the RPT device 4000 applies a "compliance model" to the therapy summary data to compute the SPS, and transmits the SPS to the therapy management server 220 along with the therapy summary data.

In other implementations, the therapy management server 220 applies a compliance model to the therapy summary data to compute the SPS at step 320 before applying the rule set(s).

The compliance model may take into account other data relating to the patient, such as profile data, physiological data, and electronic medical record (EMR) data. The profile data may include demographic data such as patient age, sex, marital status, weight, occupation, address, education level, and nationality, and the primary care physician who prescribed the respiratory pressure therapy. The profile data may also include details of the prescribed respiratory pressure therapy, such as type and model of the RPT device 4000, the initial settings of the RPT device 4000, and type, model, and size of patient interface 3000 to be used. The EMR data typically contains a medical history of the patient including previous conditions, treatments, co-morbidities, and current status.

One example of a compliance model is described below.

One example of an "at risk" rule is "7 day at risk". In one implementation of the "7 day at risk" rule using a numerically-valued SPS, the condition is "After 7 days, SPS is less than a threshold", where in one example the threshold is 25%. In another implementation of the "7 day at risk" rule using a label-valued SPS, the condition is "After 7 days, SPS is 'very unlikely' or 'unlikely'". Such rules include a time-based element as well as a dependence on the SPS. Other "at risk" rules have no time-based element, but simply apply to all patients whose current SPS value satisfies a condition. An example of such a rule condition is "SPS is less than a threshold." Such a rule captures any patients having an SPS less than a defined threshold at any given time.

A rule may also comprise an automatic action to be carried out by the therapy management server 220 if the condition is satisfied. For example, an automatic action could be to send a notification to the patient with some educational or motivational content. The notification could be in the form of an e-mail, an SMS message, an automated voice call, a notification within the patient app 280, or in some other modality that is computer-implementable. Such a notification should comply with any PHI/PH privacy requirements. One example of a rule comprising a condition and an automatic action is "If usage is less than four hours for three days out of a five-day period [condition], send a notification to the patient reminding them that adhering to their prescribed CPAP therapy is the key to feeling healthy [action]."

An automatic action could also be to remove a patient from a workflow group. For example, a rule such as "14 day at risk" could comprise an automatic action to remove the patient from the "7 day at risk" workflow group if they have not already been manually removed from that workflow group. In this way, the same patient would only appear in one workflow group with a time-based condition at a time.

There are several scenarios in relation to rule sets within the patient management system 200. For example, a single rule set may be applied that is common to all patients. In another scenario, each DME may have a rule set common to all patients being managed by the DME. In yet another scenario, each payor may have a specific rule set common to all patients associated with the payor. Furthermore, in some scenarios, specific rule sets may be applied to different patients based on patient characteristics or previous compliance results.

In each scenario, the rule set applicable to a patient may change depending on how long the patient has been receiving therapy. For example, a patient may start therapy on an "initial compliance" rule set (common to all patients or specific to the DME or payor associated with the patient as above). If compliant after 90 days on therapy, or other period specified by the initial compliance rule set, the patient is migrated to an "ongoing compliance" rule set (again, common to all patients or specific to the DME or payor associated with the patient as above).

Regardless of which scenario applies to the patient management system 200, for each set of therapy summary data received at step 310, step 320 applies the rule set corresponding to the patient from whom the therapy summary data originated on the date corresponding to the therapy summary data.

As mentioned above, at step 330, the patient therapy management server 220 updates a therapy management database representing the workflow groups. The therapy management database is used by a server program 245 running on the therapy management server 220 to communicate with the computing device 270 of the DME agent 260. In one implementation, the therapy management server program 245 is a web server that serves a therapy management web site. In such an implementation, the client program running on the computing device 270 that interacts with the therapy management server 220 is a browser. In another implementation, the client program running on the computing device 270 is a custom-designed "app" that interacts in client-server fashion with a custom-designed therapy management server program. In either case, the therapy management server program 245 serves a graphical layout representing the workflow groups, as described in more detail below with reference to FIGS. 4 to 13.

At the next step 340, the therapy management server 220 determines whether to transmit a notification to the computing device 270 associated with the DME agent 260. The notification prompts the DME agent 260 to log in to the therapy management server program 245. Step 340 may take into account whether step 320 in the current execution of the method 300 sent a notification to a patient for whose therapy the DME agent 260 is responsible. Alternatively, or additionally, step 340 may take into account whether a notification has been sent to a patient for whose therapy the DME agent 260 is responsible since the DME agent 260 last logged in to the therapy management server program 245. For example, if a notification has been sent to a patient since the DME agent 260 last logged in, step 340 returns in the affirmative.

If the determination in step 340 is negative ("N"), the method 300 concludes at step 360. If the determination in step 340 is affirmative ("Y"), at step 350 a notification is transmitted to the computing device 270 associated with the DME agent 260 to prompt the DME agent 260 to log in to the therapy management server program 245. The notification may be an e-mail, an SMS message, an automated voice call, or in some other modality that is computer-implementable. The method 300 then concludes at step 360.

Compliance Model

As mentioned above, in some implementations of the method 300, step 320 of the method 300 applies a compliance model to compute the SPS. One implementation of a compliance model is a linear predictive model, which computes the SPS as a weighted sum of its N input feature values $f_1, \ldots, f_N$ (drawn from the therapy summary data and other input data), plus a constant C:

$$SPS = C + \sum_{n=1}^{N} c_n f_n \qquad (1)$$

The $c_n$ are the weighting coefficients for the respective feature values $f_n$. The SPS computed according to equation (1) may be mapped to the range [0, 1] by means of a function such as the sigmoid or the inverse tangent.

In other implementations of the step 320, the compliance model may be a neural network, decision tree ensemble, support vector machine, Bayesian network, or gradient boosting machine. Such structures can be configured to implement either linear or non-linear predictive models.

The parameters of the compliance model, such as (in the linear predictive model) the coefficients $c_n$ and the constant C, may be obtained from training carried out using historical input data according to conventional predictor training methods. In some implementations of step 320, the compliance model parameters are altered between executions of the method 300, for example to increase or decrease the weighting coefficient of a certain feature value as therapy proceeds, according to a predetermined schedule. For example, during the first five days of therapy, the average usage time per session may be the most important feature, while later on, other factors (such as how many sessions has the patient already been compliant) may have a higher weighting.

Therapy Management Graphical Layout

Figure 4:

In one implementation of the patient management system 200, upon the DME agent 260 logging into the therapy management server program, the therapy management server program 245 draws on the therapy management database to serve a graphical layout representing the workflow groups to the computing device 270 associated with the DME agent 260. FIG. 4 contains an example 400 of such a graphical layout. Each text heading in the graphical layout 400, such as the text heading 410, represents a workflow group containing one or more patients. The text heading 410 summarises the rule associated with the workflow group (e.g. "7 day at risk" in the case of heading 410, summarising the rule "After 7 days, patient is at risk of not being compliant"). Beneath the text heading 410 is a number 420, indicating the number of patients in the workflow group, i.e. the number of patients satisfying the associated rule. For example, the number 420 is 4, indicating that 4 patients currently satisfy the "7 day at risk" rule.

The graphical layout 400 presents the therapy summary data to the DME agent 260 in a manner that emphasises where potential problems lie and thus where attention is most needed. Previous patient management systems had access to the same therapy summary data, but presented it to the DME agent in a manner that made it much less convenient for the DME agent to identify which patients needed attention most urgently. The display of each group associated with an incomplete workflow reinforces to the DME agent that manual action needs to be taken for the patients in the group, and the group remains prominently featured on the graphical layout 400 until all the manual actions specified by the workflow are complete.

Figure 5:
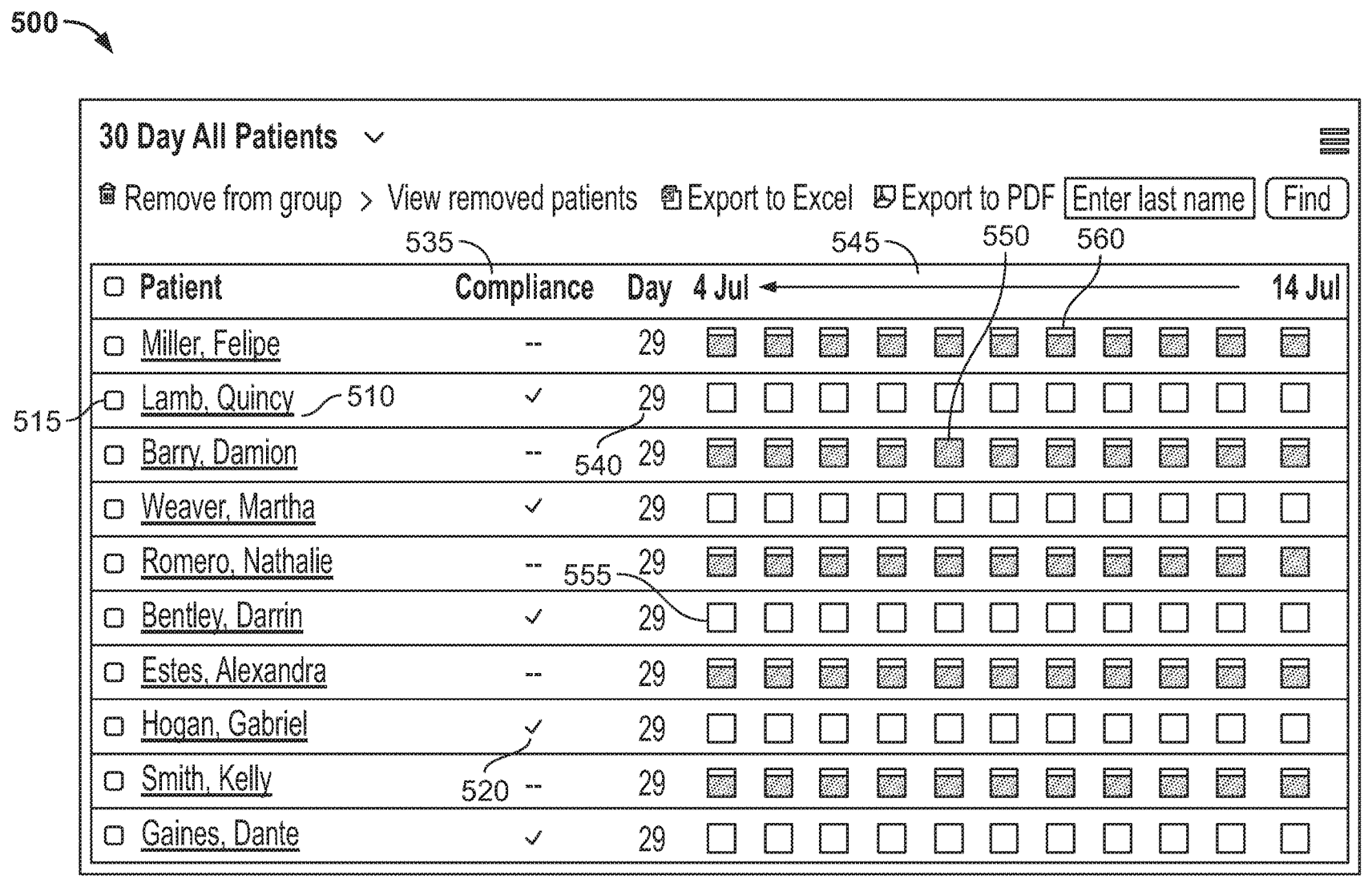

Upon activating, e.g. by clicking a pointing device of the computing device 270 on, a text heading 410 in the graphical layout 400, the DME agent 260 is served with a workflow group layout, such as the workflow group layout 500 illustrated in FIG. 5, containing details of the patients in the workflow group associated with the activated text heading. The workflow group layout 500 lists the patients in the '30 day all patients' workflow group, with each patient, e.g. 510, occupying a row of the workflow group layout 500. If there are too many patients in the group to fit in one screen of the computing device 270, the display of the workflow group layout 500 may be "scrolled" to reveal more patients in the group.

The patients in an "at risk" group may be ranked within the group so as to prioritise, for the DME agent 260, those patients for whom a manual action is most "needed" according to some statistic obtained from the compliance model (e.g., based on the SPS). In one example, the ranking statistic is the SPS itself. In another example, the ranking statistic is the probability of the patient becoming compliant after an engagement, that is, the SPS re-computed under the assumption that an engagement has already taken place (the SPS after engagement). Another example of a ranking statistic, which indicates the benefit of an engagement with the patient, is the difference between the SPS after engagement and the SPS prior to engagement. In yet another example, which indicates the benefit/cost ratio of an engagement with the patient, the ranking statistic is the difference between the SPS after engagement and the SPS prior to engagement, divided by the product of the SPS prior to engagement and the cost of an engagement.

The columns of each row in the workflow group layout 500 contain the name of the associated patient 510 and properties of the therapy of the associated patient 510.

A double dot in the column 535 headed "Compliance" indicates that the patient's usage does not comply with the predetermined compliance standard, while a check mark, e.g. 520, indicates the opposite. A dash indicates that sufficient data concerning the patient's usage is not yet available from the patient to apply the predetermined compliance standard. The column headed "Day" contains a number (e.g. 540) indicating the number of days (29, for the number 540) since the patient started therapy.

The columns beneath the date range 545 contain a series of therapy icons, e.g. 550, each therapy icon visually indicating properties of a corresponding therapy session, ordered by date from left to right. The endpoints of the date range 545 are the endpoints of the range of therapy sessions covered by the therapy icons 550. A generally dark filled therapy icon, e.g. 550, indicates that the patient's usage for that session was below a threshold duration, e.g. 4 hours. A light filled therapy icon, e.g. 555, indicates that the patient's usage for that session was above the threshold duration. An unfilled therapy icon indicates that no data is available for the patient for the corresponding date.

A therapy icon may also indicate two other properties of the therapy session. If the therapy icon contains a light-coloured overbar, e.g. 560, the AHI for the therapy session exceeded a threshold. If the therapy icon contains a light-coloured underbar (not shown), the average leak flow rate for the therapy session exceeded a threshold.

A control 515, e.g. a checkbox, displayed to the left of the patient's name 510 may be activated (e.g. checked) by the DME agent 260. The activation of the control causes the therapy management server 220 to remove the patient from the workflow group. The workflow group layout 500 therefore offers a convenient means for the DME agent 260 to manage the therapy of his or her patients according to predefined workflows. The patients subject to a particular workflow are automatically identified and presented to the DME agent 260 in a convenient tabular format, along with certain properties of their recent therapy in graphic form. Once any manual action specified by the workflow has been taken in relation to a particular patient, the DME agent 260 may manually remove the patient from the workflow group by activating the control 515. The DME agent may also, or alternatively, add a note to the patient at this time, as described in more detail below, which records the manual action taken and/or the result of the manual action.

Figure 6:
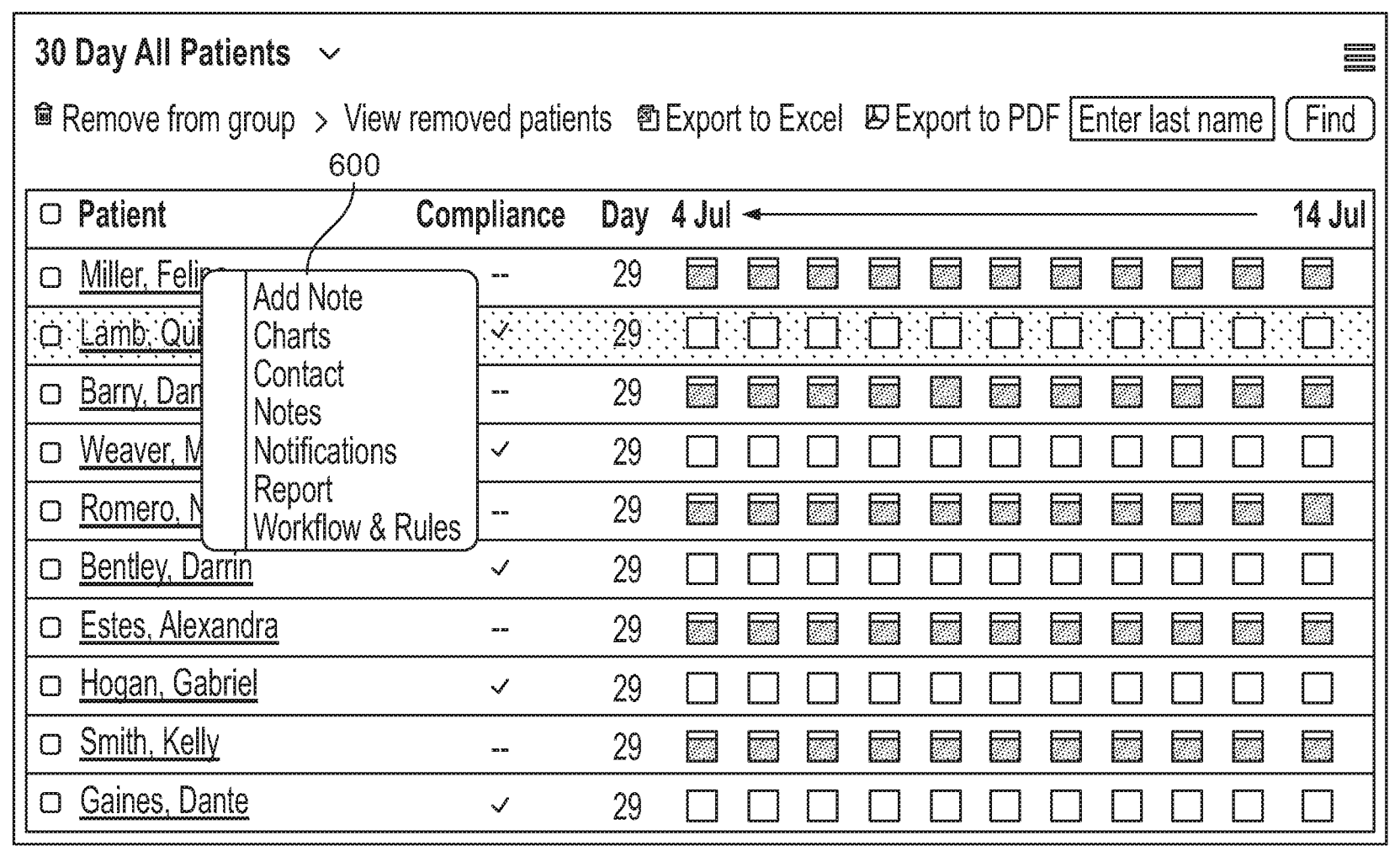

Activating, e.g. by clicking a pointing device of the computing device 270 on, the patient name 510 of a patient in the workflow group layout 500, brings up a "patient menu", e.g. the patient menu 600 illustrated in FIG. 6. The patient menu 600 contains various options relating to the patient associated with the activated name. Each menu option may be activated, e.g. by clicking the pointing device of the computing device 270 on it.

Figure 7:
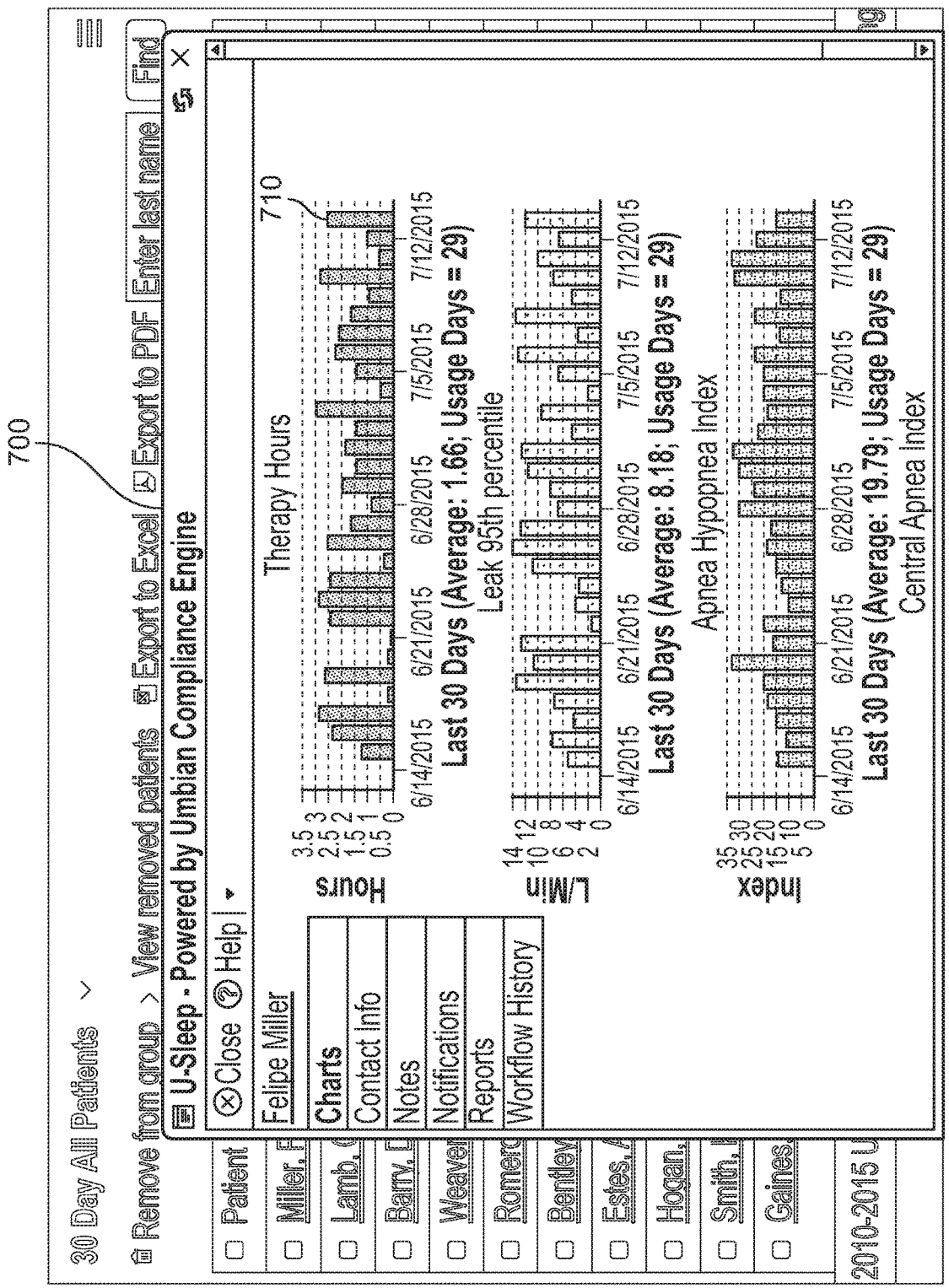

Activating the "Charts" option in the patient menu 600 brings up a chart, e.g. the chart 700 illustrated in FIG. 7. The chart 700 visually represents the recent history of the therapy of the patient. The rows of the chart 700 correspond to different therapy properties for a session, e.g. (from top to bottom in the chart 700) usage, leak flow rate, and AHI. Each row contains a graph, e.g. 710, representing the time profile of the corresponding therapy property over some recent period, e.g. (as in the chart 700) the most recent 30 days.

Figure 8:
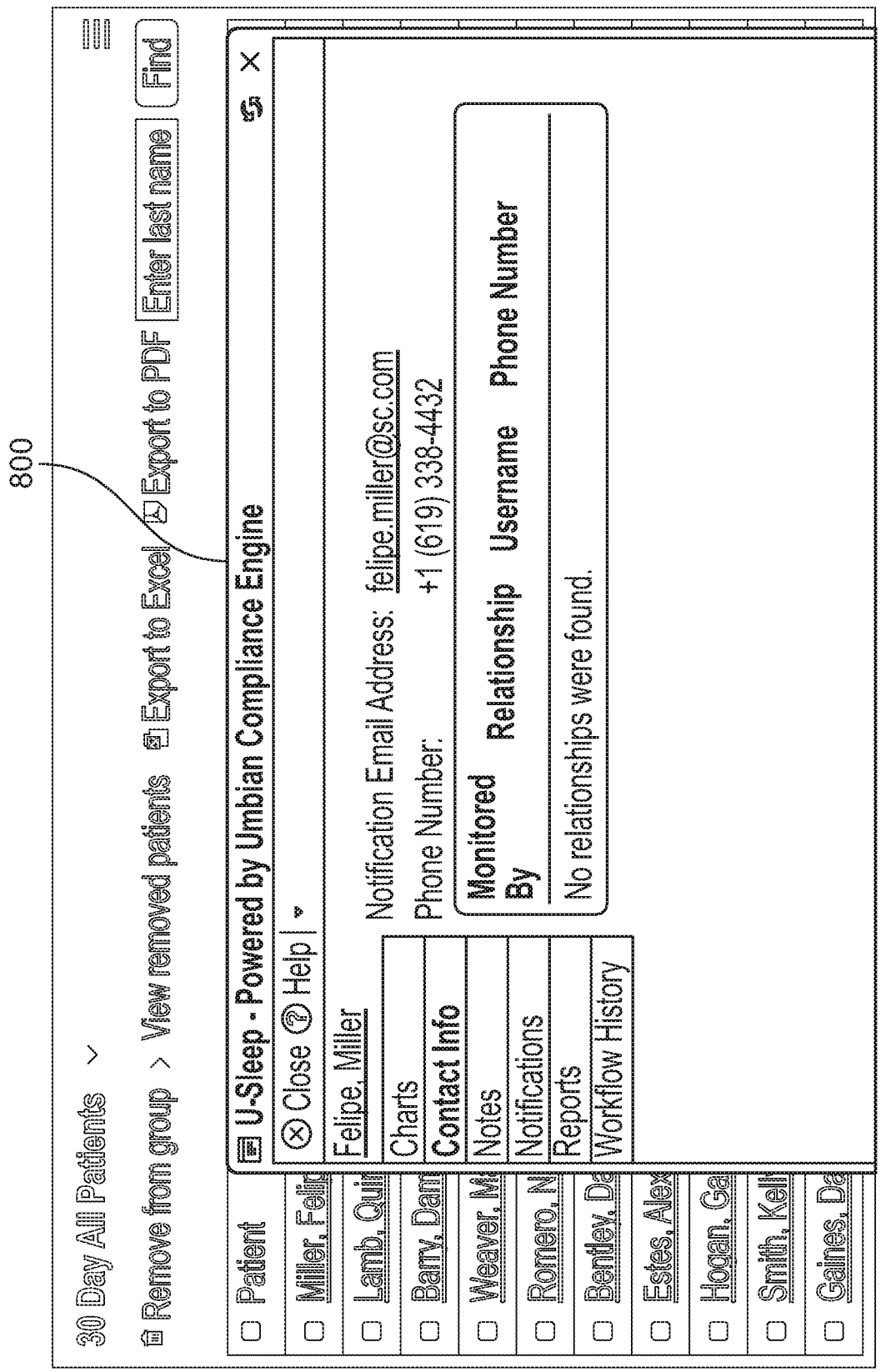
Figure 10:
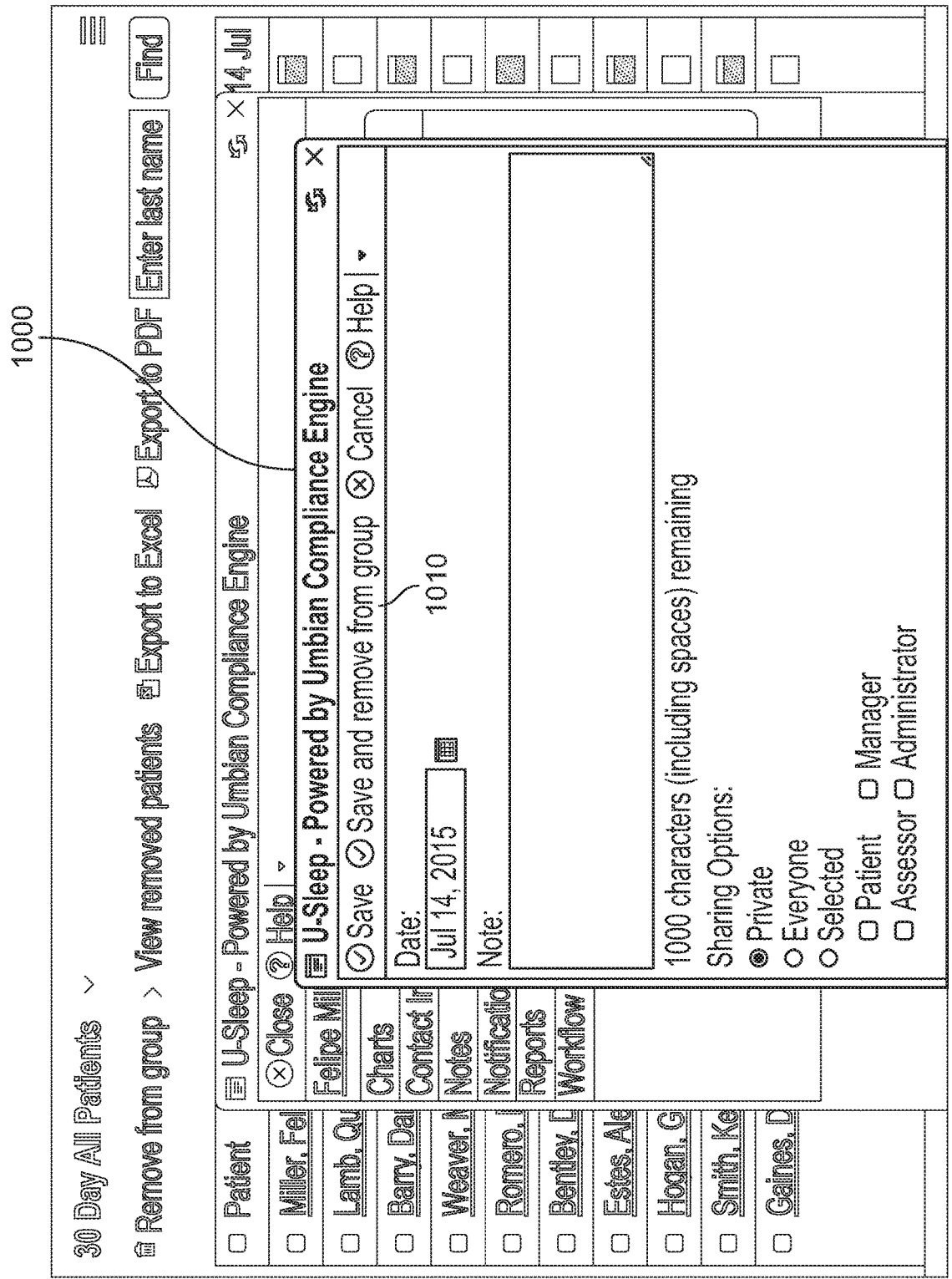

Activating the "Contact info" option in the patient menu 600 brings up a "contact window" 800 illustrated in FIG. 8, containing contact details for the patient, to assist the DME agent in contacting the patient, as may be required for a particular workflow.

Figure 9:
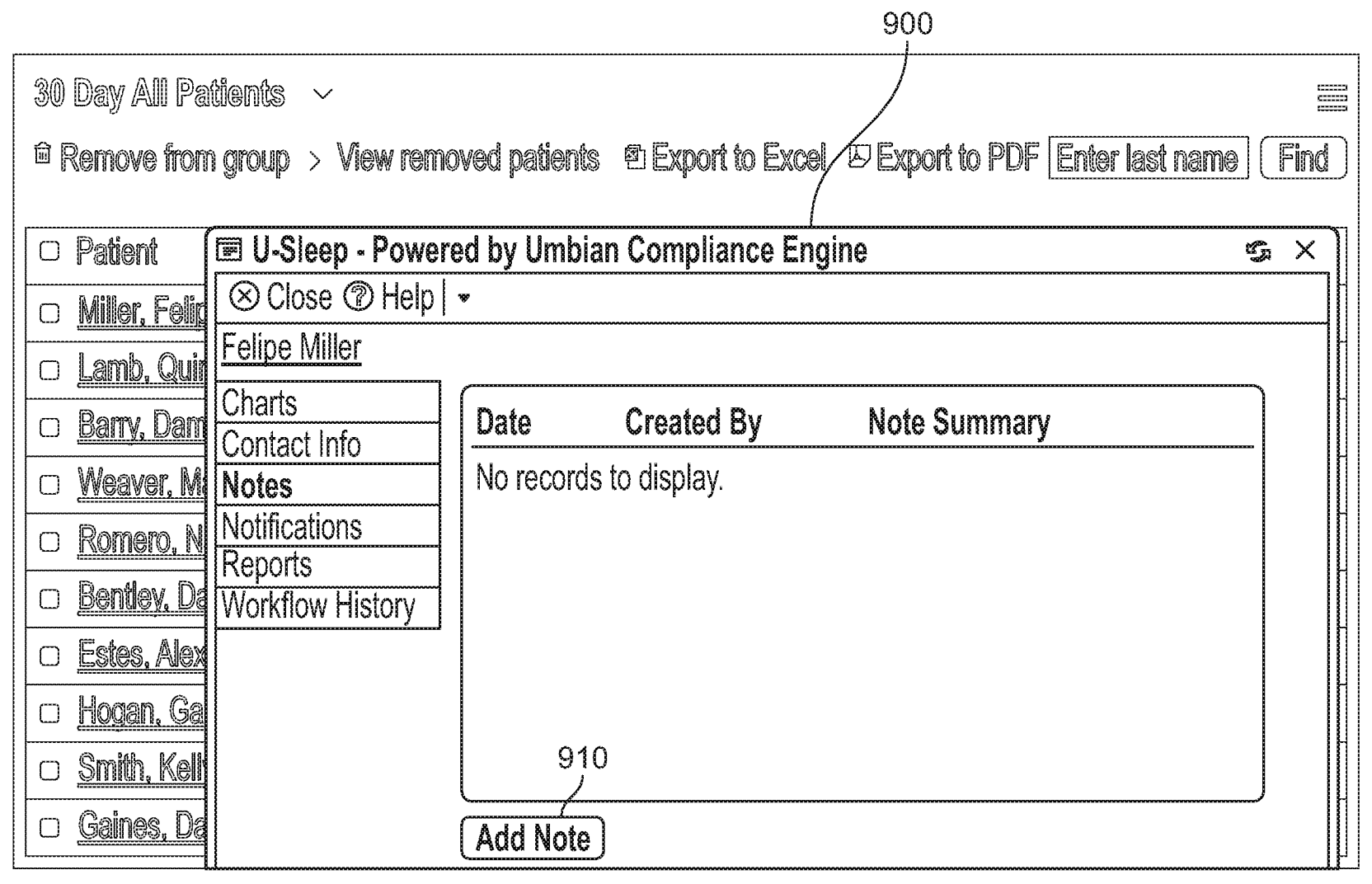

Activating the "Notes" option in the patient menu 600 brings up a "notes window" 900 illustrated in FIG. 9. The notes window 900 contains a table, each row of which corresponds to a note that has been added in relation to the patient. The columns of a row indicate properties of the associated note, e.g. its creator, creation date, and a summary of the contents of the note. Clicking the pointing device of the computing device 270 on the "add note" control 910 brings up a "new note window" 1000 illustrated in FIG. 10. The new note window 1000 allows the DME agent to set the properties of a new note for the patient, including a date, the contents of the note, and certain sharing options specifying who may view the note. In one example, the DME agent may add a note when he or she has contacted the patient in accordance with a manual action specified by the workflow associated with the rule that was satisfied by the patient to bring him or her to the attention of the DME agent. In such an example, the DME agent may activate the "Save and remove from group" control 1010 to save the note and remove the patent from the workflow group. This is an alternative way of removing a patient from a workflow group to the use of the control 515.

Figure 11:
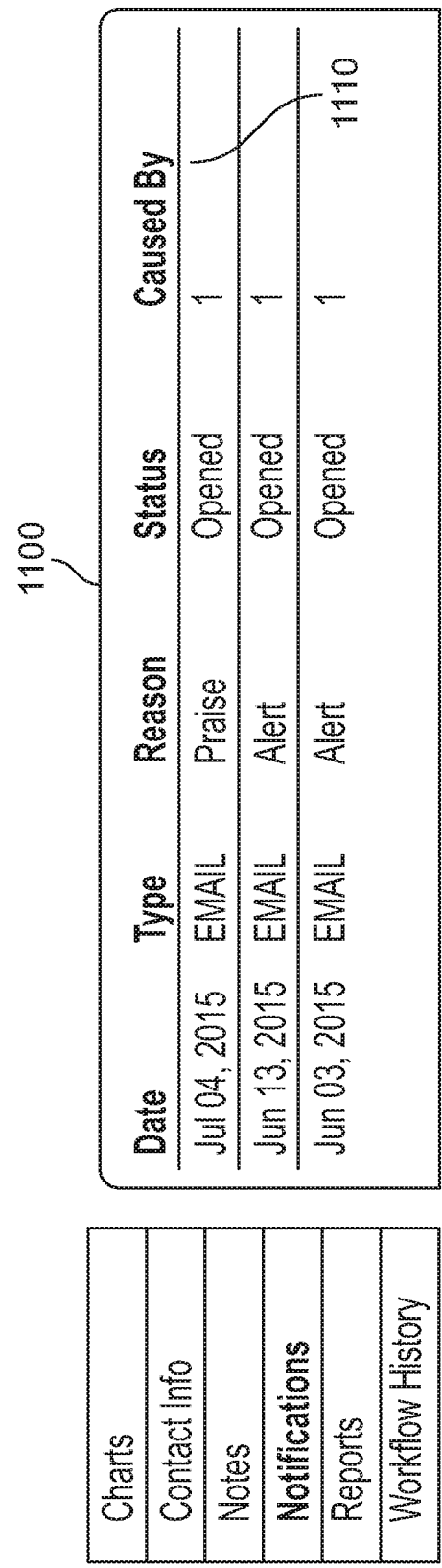

Activating the "Notifications" option in the patient menu 600 brings up a "notifications window" 1100 illustrated in FIG. 11. The notifications window 1100 contains a table, each row of which, e.g. 1110, corresponds to a notification that has been transmitted to a patient as a result of a rule application, as described above in relation to step 320. The columns of the row 1110 indicate properties of the associated notification, e.g. its date, type, reason, status (i.e. whether it has been opened by the patient), and which rule the notification resulted from (in the case of all notifications in the notifications window 1100, that rule is rule 1).

Figure 12:
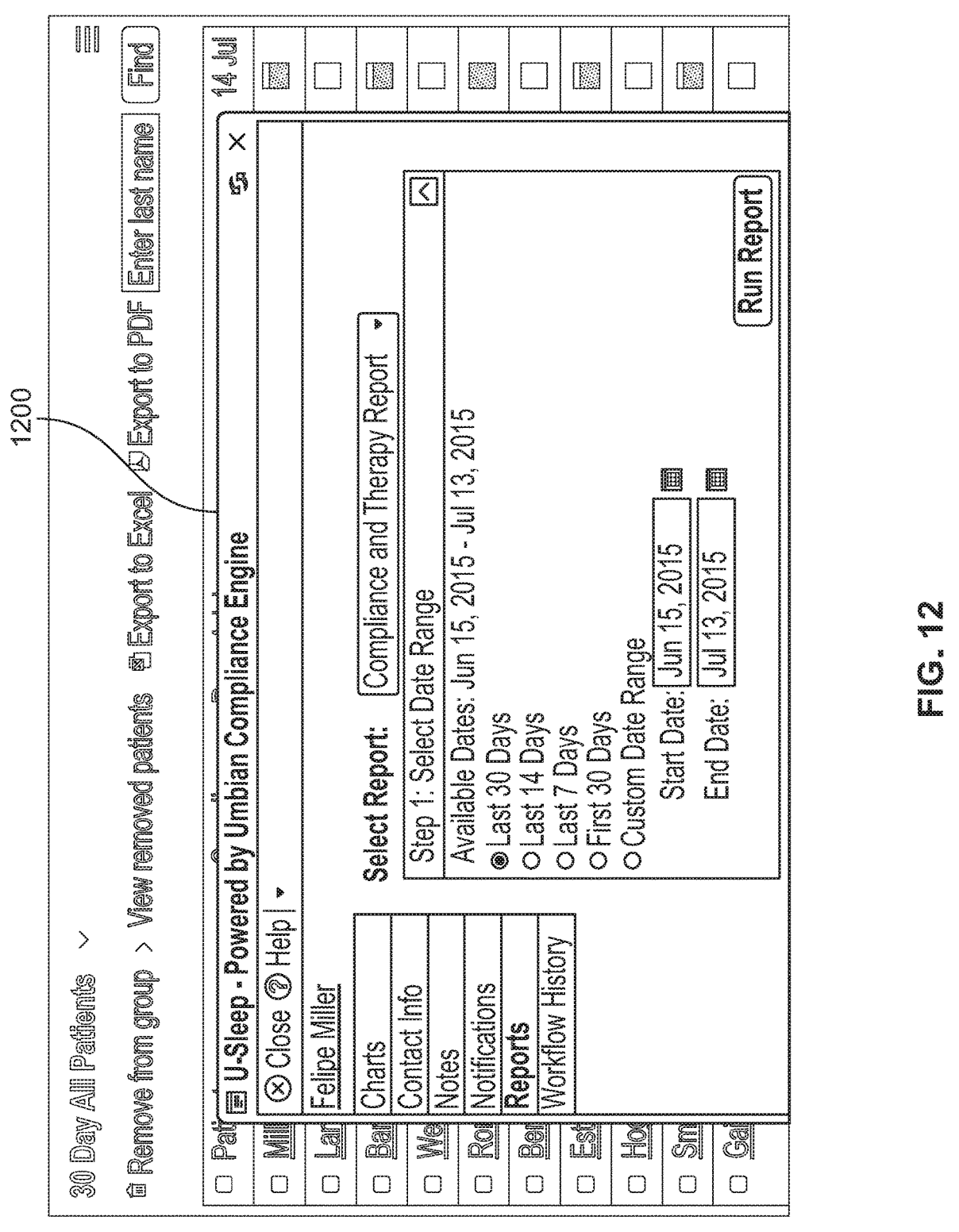

Activating the "Reports" option in the patient menu 600 brings up a "reports window" 1200 illustrated in FIG. 12. The reports window 1200 contains an interface to allow the DME agent to generate a report summarising the patient's therapy. The reports window 1200 illustrates the first step in a multi-step report generation procedure, namely a "select date range" step.

Figure 13:
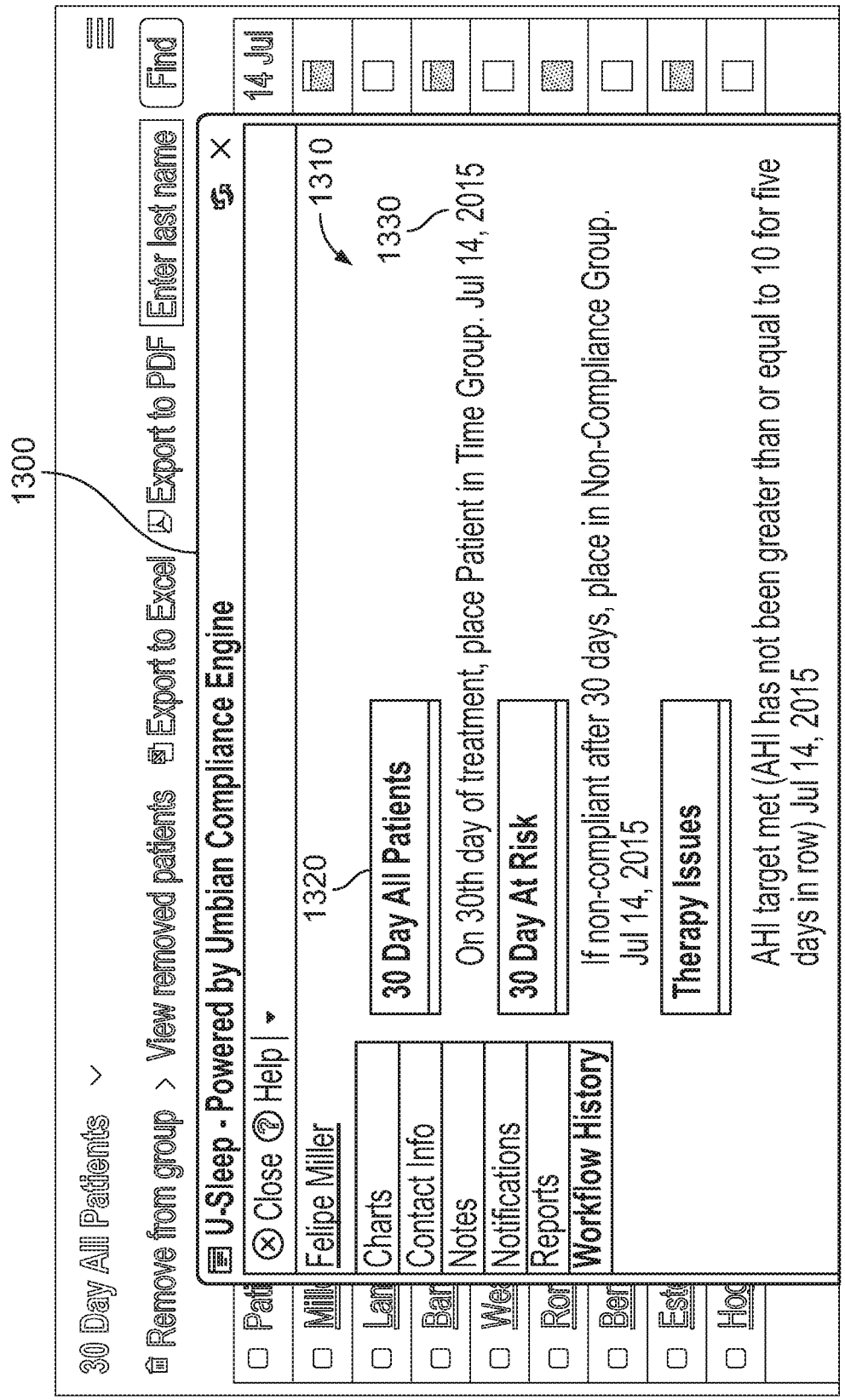

Activating the "Workflow history" option in the patient menu 600 brings up a "workflow history window" 1300 illustrated in FIG. 13. The workflow history window 1300 contains a list of workflow groups to which the patient has previously been added. Each entry in the list, e.g. the entry 1310, contains an icon, e.g. 1320, indicating the name of the workflow group to which the patient has been added, e.g. "30 Day All Patients" in the case of the icon 1320, and the date 1330 on which the patient was added to the workflow group. If the patient were no longer in the workflow group, the entry 1310 would also contain the date on which the patient was removed from the workflow group, and the name of the DME agent 260 who removed the patient from the workflow group. The workflow history window thus allows the DME agent to review at a glance the history of the patient's additions to and removals from various workflow groups, and thus gain a rapid understanding of the progress of the patient's therapy.

Glossary

For the purposes of the present technology disclosure, in certain forms of the present technology, one or more of the following definitions may apply. In other forms of the present technology, alternative definitions may apply.

General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Continuous Positive Airway Pressure (CPAP) therapy: CPAP therapy will be taken to mean the application of a supply of air to the entrance to the airways in which the treatment pressure is continuously positive with respect to atmosphere, and preferably approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Automatic Positive Airway Pressure (APAP) therapy: CPAP therapy in which the treatment pressure is continually automatically adjustable, e.g. from breath to breath, between minimum and maximum limits, depending on the presence or absence of indications of SDB events.

Patient: A person, whether or not they are suffering from a respiratory condition.

Aspects of the Respiratory Cycle

Apnea: Preferably, apnea will be said to have occurred when flow falls below a predetermined threshold rate for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): Breathing effort will be said to be the work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Hypopnea: Preferably, a hypopnea will be taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort.

Hyperpnea: An increase in flow to a level higher than normal flow rate.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, airflow rate, patient airflow rate, respiratory airflow rate (Qr): These synonymous terms may be understood to refer to the RPT device's estimate of respiratory airflow rate, as opposed to "true respiratory flow" or "true respiratory airflow", which is the actual respiratory flow rate experienced by the patient, usually expressed in litres per minute.

Tidal volume (Vt): The volume of air inhaled or exhaled during normal breathing, when extra effort is not applied.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of the inspiratory portion of one respiratory flow rate waveform and the start of the inspiratory portion of the following respiratory flow rate waveform.

Typical recent ventilation: The value of ventilation around which recent values over some predetermined timescale tend to cluster, that is, a measure of the central tendency of the recent values of ventilation.

Upper airway obstruction (UAO): includes both partial and total upper airway obstruction. This may be associated with a state of flow limitation, in which the level of flow increases only slightly or may even decrease as the pressure difference across the upper airway increases (Starling resistor behaviour).

Ventilation (Vent): A measure of the total amount of gas being exchanged by the patient's respiratory system, including both inspiratory and expiratory flow, per unit time. When expressed as a volume per minute, this quantity is often referred to as "minute ventilation". Minute ventilation is sometimes given simply as a volume, understood to be the volume per minute.

RPT Device Variables

Flow rate: The instantaneous volume (or mass) of air delivered per unit time. While flow rate and ventilation have the same dimensions of volume or mass per unit time, flow rate is measured over a much shorter period of time. In some cases, a reference to flow rate will be a reference to a scalar quantity, namely a quantity having magnitude only. In other cases, a reference to flow rate will be a reference to a vector quantity, namely a quantity having both magnitude and direction. Where it is referred to as a signed quantity, a flow rate may be nominally positive for the inspiratory portion of a breathing cycle of a patient, and hence negative for the expiratory portion of the breathing cycle of a patient. Flow rate will be given the symbol Q. 'Flow rate' is sometimes shortened to simply 'flow'. Total flow rate, Qt, is the flow rate of air leaving the RPT device. Vent flow rate, Qv, is the flow rate of air leaving a vent to allow washout of exhaled gases. Leak flow rate, Ql, is the flow rate of unintentional leak from a patient interface system. Respiratory flow rate, Qr, is the flow rate of air that is received into the patient's respiratory system.

Leak: The word leak will be taken to be a flow of air to the ambient. Leak may be intentional, for example to allow for the washout of exhaled $CO_2$. Leak may be unintentional, for example, as the result of an incomplete seal between a mask and a patient's face. In one example leak may occur in a swivel elbow.

Pressure: Force per unit area. Pressure may be measured in a range of units, including $cmH_2O$, $g-f/cm^2$, hectopascal. 1 $cmH_2O$ is equal to 1 $g-f/cm^2$ and is approximately 0.98 hectopascal. In this specification, unless otherwise stated, pressure is given in units of $cmH_2O$. The pressure in the patient interface is given the symbol Pm, while the treatment pressure, which represents a target value to be achieved by the mask pressure Pm at the current instant of time, is given the symbol Pt.

Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

8.4 REFERENCE SIGNS LIST

| | |
|---|---|
| patient | 100 |
| bed partner | 110 |
| patient management system | 200 |
| data server | 210 |
| therapy management server | 220 |
| network | 230 |
| therapy management process | 240 |
| therapy management server program | 245 |
| patient computing device | 250 |
| DME agent | 260 |
| computing device | 270 |
| patient app | 280 |
| method | 300 |
| step | 310 |
| step | 320 |
| step | 330 |
| step | 340 |
| step | 360 |
| graphical layout | 400 |
| heading | 410 |
| number | 420 |
| workflow group layout | 500 |
| patient | 510 |
| control | 515 |
| column | 535 |
| number | 540 |
| date range | 545 |
| therapy icons | 550 |
| patient menu | 600 |
| chart | 700 |
| notes window | 900 |
| control | 910 |
| new note window | 1000 |
| control | 1010 |
| notifications window | 1100 |
| row | 1110 |
| reports window | 1200 |
| workflow history window | 1300 |
| entry | 1310 |
| icon | 1320 |
| date | 1330 |
| patient interface | 3000 |
| RPT device | 4000 |
| air circuit | 4170 |
| humidifier | 5000 |

FURTHER EXAMPLES OF THE TECHNOLOGY

The following paragraphs further illustrate examples of the present technology described herein.

Example 1

A patient management system comprising: a data server in communication with a plurality of respiratory pressure therapy devices, wherein the respiratory pressure therapy devices are each configured to deliver respiratory pressure therapy to a patient, and to generate therapy data relating to a session of respiratory pressure therapy, the data server being configured to compute, from the therapy data, therapy summary data for the session, the therapy summary data comprising one or more statistics summarising the therapy data; and a therapy management server in communication with the data server, the therapy management server being configured to: apply one or more rules to the therapy summary data; update one or more workflow groups of patients, each workflow group corresponding to a rule, depending on results of the respective rule applications; and serve a graphical layout representing the one or more workflow groups.

Example 2

A patient management system according to Example 1, wherein the therapy management server is further configured, upon activation of a workflow group in the graphical layout, to serve a graphical layout containing details of the patients in the workflow group.

Example 3

A patient management system according to Example 2 (or any one of the preceding Examples), wherein the details of the patients in the workflow group comprise a name of a patient in the workflow group.

Example 4

A patient management system according to Example 3 (or any one of the preceding Examples), wherein the therapy management server is further configured, upon activation of the name of the patient in the workflow group, to serve a patient menu comprising one or more options relating to the patient.

Example 5

A patient management system according to Example 4 (or any one of the preceding Examples), wherein one option is a workflow history option, and the therapy management server is further configured, upon activation of the workflow history option, to serve a list of workflow groups to which the patient has previously been added.

Example 6

A patient management system according to Example 5 (or any one of the preceding Examples), wherein each entry of the list comprises the name of a workflow group to which the patient has previously been added, and the date on which the patient was added to the workflow group.

Example 7

A patient management system according to any one of Examples 2-6 (or any one of the preceding Examples), wherein the details of the patients in the workflow group comprise a control associated with a patient in the workflow group, and the therapy management server is further configured, upon activation of the control, to remove the associated patient from the workflow group.

Example 8

A patient management system according to any one of Examples 1-7 (or any one of the preceding Examples), wherein a rule comprises a condition that is applicable to one or more features of the therapy summary data.

Example 9

A patient management system according to Example 8 (or any one of the preceding Examples), wherein updating the one or more workflow groups comprises adding a patient to a workflow group upon the one or more features of the therapy summary data satisfying the condition comprised by the rule corresponding to the workflow group.

Example 10

A patient management system according to Example 8 (or any one of the preceding Examples), wherein a rule further comprises an action to be carried out upon the condition being satisfied.

Example 11

A patient management system according to Example 10 (or any one of the preceding Examples), wherein the action comprises sending a notification to the patient.

Example 12

A patient management system according to any one of Examples 1-11 (or any one of the preceding Examples), wherein the therapy management server is further configured to determine whether to transmit a notification to a computing device.

Example 13

A patient management system according to Example 12 (or any one of the preceding Examples), wherein the therapy management server is further configured to transmit the notification to the computing device based on the determination.

Example 14

A patient management system according to any one of Examples 1-13 (or any one of the preceding Examples), wherein the data server is coincident with the therapy management server.

Example 15

The patient management system according to any one of Examples 1-14 (or any one of the preceding Examples), further comprising the plurality of respiratory pressure therapy devices.

Example 16

A patient management system comprising: a therapy management server in communication with a respiratory pressure therapy device, wherein the respiratory pressure therapy device is configured to deliver respiratory pressure therapy to a patient during a session and to compute, from therapy data relating to a session of respiratory pressure therapy, therapy summary data for the session, the therapy summary data comprising one or more statistics summarising the therapy data, the therapy management server being configured to: apply one or more rules to the therapy summary data; update one or more workflow groups, each workflow group corresponding to a rule, depending on results of the respective rule applications; and serve a graphical layout representing the one or more workflow groups.

Example 17

A patient management system according to Example 16 (or any one of the preceding Examples), wherein the therapy management server is further configured, upon activation of a workflow group in the graphical layout, to serve a graphical layout containing details of the patients in the workflow group.

Example 18

A patient management system according to Example 17 (or any one of the preceding Examples), wherein the details of the patients in the workflow group comprise a name of a patient in the workflow group.

Example 19

A patient management system according to Example 18 (or any one of the preceding Examples), wherein the therapy management server is further configured, upon activation of the name of the patient in the workflow group, to serve a patient menu comprising one or more options relating to the patient.

Example 20

A patient management system according to Example 19 (or any one of the preceding Examples), wherein one option is a workflow history option, and the therapy management server is further configured, upon activation of the workflow history option, to serve a list of workflow groups to which the patient has previously been added.

Example 21

A patient management system according to Example 20 (or any one of the preceding Examples), wherein each entry of the list comprises the name of a workflow group to which the patient has previously been added, and the date on which the patient was added to the workflow group.

Example 22

A patient management system according to any one of Examples 17-21 (or any one of the preceding Examples), wherein the details of the patients in the workflow group comprise a control associated with a patient in the workflow group, and the therapy management server is further configured, upon activation of the control, to remove the associated patient from the workflow group.

Example 23

A patient management system according to any one of Examples 16-22 (or any one of the preceding Examples),
wherein a rule comprises a condition that is applicable to one or more features of the therapy summary data.

Example 24

A patient management system according to Example 23 (or any one of the preceding Examples), wherein updating the one or more workflow groups comprises adding the patient to a workflow group upon the one or more features of the therapy summary data satisfying the condition comprised by the rule corresponding to the workflow group.

Example 25

A patient management system according to Example 23 (or any one of the preceding Examples), wherein a rule further comprises an action to be carried out if the condition is satisfied.

Example 26

A patient management system according to Example 25 (or any one of the preceding Examples), wherein the action comprises sending a notification to the patient.

Example 27

A patient management system according to any one of Examples 16-26 (or any one of the preceding Examples), wherein the therapy management server is further configured to determine whether to transmit a notification to a computing device.

Example 28

A patient management system according to Example 27 (or any one of the preceding Examples), wherein the therapy management server is further configured to transmit the notification to the computing device.

Example 29

The patient management system according to any one of Examples 16-28 (or any one of the preceding Examples) further comprising a plurality of the respiratory pressure therapy devices.

Example 30

A method of managing one or more patients undergoing respiratory pressure therapy, the method comprising: applying, by a therapy management server, one or more rules to therapy summary data comprising one or more statistics summarising therapy data relating to a session of respiratory pressure therapy for a patient; updating, by the therapy management server, one or more workflow groups, each workflow group corresponding to a rule, depending on results of the respective rule applications; and serving, by the therapy management server, a graphical layout representing the one or more workflow groups.

Example 31

A method according to Example 30 (or any one of the preceding Examples), further comprising, upon activation of a workflow group in the graphical layout, serving a graphical layout containing details of the patients in the workflow group.

Example 32

A method according to Example 31 (or any one of the preceding Examples), wherein the details of the patients in the workflow group comprise a name of a patient in the workflow group.

Example 33

A method according to Example 32 (or any one of the preceding Examples), further comprising, upon activation of the name of the patient in the workflow group, serving a patient menu comprising one or more options relating to the patient.

Example 34

A method according to Example 33 (or any one of the preceding Examples), wherein one option is a workflow history option, the method further comprising, upon activation of the workflow history option, serving a list of workflow groups to which the patient has previously been added.

Example 35

A method according to Example 34 (or any one of the preceding Examples), wherein each entry of the list comprises the name of a workflow group to which the patient has previously been added, and the date on which the patient was added to the workflow group.

Example 36

A method according to any one of Examples 31-35 (or any one of the preceding Examples), wherein the details of the patients in the workflow group comprise a control associated with a patient in the workflow group, the method further comprising, upon activation of the control, removing the associated patient from the workflow group.

Example 37

A method according to any one of Examples 30-36 (or any one of the preceding Examples), wherein a rule comprises a condition that is applicable to one or more features of the therapy summary data.

Example 38

A method according to Example 37 (or any one of the preceding Examples), wherein the updating comprises adding the patient to a workflow group upon the one or more features of the therapy summary data satisfying the condition comprised by the rule corresponding to the workflow group.

Example 39

A method according to Example 37 (or any one of the preceding Examples), wherein a rule further comprises an action to be carried out if the condition is satisfied.

Example 40

A method according to Example 39 (or any one of the preceding Examples), wherein the action comprises sending a notification to the patient.

Example 41

A method according to any one of Examples 30-40 (or any one of the preceding Examples), further comprising determining, by the therapy management server, whether to transmit a notification to a computing device.

Example 42

A method according to Example 41 (or any one of the preceding Examples), further comprising transmitting, by the therapy management server, the notification to the computing device.

Example 43

A respiratory pressure therapy management server configured to: apply one or more rules to therapy summary data comprising one or more statistics summarising therapy data relating to a session of respiratory pressure therapy for a patient; update one or more workflow groups, each workflow group corresponding to a rule, depending on results of the respective rule applications; and serve a graphical layout representing the one or more workflow groups.

Example 44

A patient management system comprising: a data server in communication with a respiratory pressure therapy device, the respiratory pressure therapy device configured to deliver respiratory pressure therapy to a patient, and generate therapy data relating to a session of respiratory pressure therapy, the data server being configured to: compute, from the therapy data, therapy summary data for the session, the therapy summary data comprising one or more statistics summarising the therapy data; and compute, from the therapy summary data, a score indicating a probability that the patient will meet a compliance standard; and a therapy management server in communication with the data server, the therapy management server being configured to: update a workflow group of patients depending on the score; and serve a graphical layout representing the workflow group.

Example 45

A patient management system according to Example 44 (or any one of the preceding Examples), wherein the therapy management server is further configured, upon activation of a workflow group in the graphical layout, to serve a graphical layout containing details of the patients in the workflow group.

Example 46

A patient management system according to Example 45 (or any one of the preceding Examples), wherein the details of the patients in the workflow group comprise a name of a patient in the workflow group.

Example 47

A patient management system according to Example 46 (or any one of the preceding Examples), wherein the therapy management server is further configured, upon activation of the name of the patient in the workflow group, to serve a patient menu comprising one or more options relating to the patient.

Example 48

A patient management system according to Example 47 (or any one of the preceding Examples), wherein one option is a workflow history option, and the therapy management server is further configured, upon activation of the workflow history option, to serve a list of workflow groups to which the patient has previously been added.

Example 49

A patient management system according to Example 48 (or any one of the preceding Examples), wherein each entry of the list comprises the name of a workflow group to which the patient has previously been added, and the date on which the patient was added to the workflow group.

Example 50

A patient management system according to any one of Examples 45-49 (or any one of the preceding Examples), wherein the details of the patients in the workflow group comprise a control associated with a patient in the workflow group, and the therapy management server is further configured, upon activation of the control, to remove the associated patient from the workflow group.

Example 51

A patient management system according to any one of Examples 44-50 (or any one of the preceding Examples) wherein the score is a numerical value representing the probability that the patient will meet the compliance standard.

Example 52

A patient management system according to Example 51 (or any one of the preceding Examples), wherein updating the workflow group comprises comparing the score with a threshold.

Example 53

A patient management system according to Example 52 (or any one of the preceding Examples), wherein updating the workflow group comprises adding the patient to the workflow group upon the score being less than or equal to the threshold.

Example 54

A patient management system according to Example 53 (or any one of the preceding Examples), wherein the therapy management server is further configured to carry out an action upon the score being less than or equal to the threshold.

Example 55

A patient management system according to Example 54 (or any one of the preceding Examples), wherein the action comprises sending a notification to the patient.

Example 56

A patient management system according to Example 55 (or any one of the preceding Examples), further comprising a computing device associated with the patient, wherein the notification is sent to the computing device associated with the patient.

Example 57

A patient management system according to Example 54 (or any one of the preceding Examples), wherein the action comprises removing a patient from a workflow group.

Example 58

A patient management system according to any one of Examples 44-57 (or any one of the preceding Examples), wherein computing the score comprises applying a compliance model to a plurality of features from the therapy summary data.

Example 59

A patient management system according to Example 58 (or any one of the preceding Examples), wherein the compliance model further takes into account profile data of the patient.

Example 60

A patient management system according to Example 52 (or any one of the preceding Examples), wherein the patient is associated with a payor, and the threshold is specific to the payor.

Example 61

A patient management system according to Example 52 (or any one of the preceding Examples), wherein the threshold is dependent on how long the patient has been receiving respiratory pressure therapy.

Example 62

A patient management system according to any one of Examples 44-61 (or any one of the preceding Examples), wherein the patients are ranked within the graphical layout of the workflow group according to a ranking statistic obtained from a compliance model.

Example 63

A patient management system according to Example 62 (or any one of the preceding Examples), wherein the ranking statistic is the score.

Example 64

A patient management system according to any one of Examples 44-63 (or any one of the preceding Examples), wherein the therapy management server is further configured to: apply one or more rules to the therapy summary data; and update one or more further workflow groups, each further workflow group corresponding to a rule, depending on results of the respective rule applications; wherein the graphical layout further represents the one or more further workflow groups.

Example 65

A patient management system according to Example 64 (or any one of the preceding Examples), wherein each further rule is one of a clinical rule, a compliance rule, and a time-based rule.

Example 66

A patient management system according to any one of Examples 44-65 (or any one of the preceding Examples), wherein the therapy management server is further configured to determine whether to transmit a notification to a computing device.

Example 67

A patient management system according to Example 66 (or any one of the preceding Examples), wherein the therapy management server is further configured to transmit the notification to the computing device based on the determination.

Example 68

A patient management system according to any one of Examples 44-67 (or any one of the preceding Examples), wherein the data server is coincident with the therapy management server.

Example 69

The patient management system according to any one of Examples 44-68 (or any one of the preceding Examples) further comprising a plurality of the respiratory pressure therapy devices.

Example 70

A patient management system comprising: a therapy management server in communication with a respiratory pressure therapy device, the respiratory pressure therapy device configured to deliver respiratory pressure therapy to a patient during a session, compute, from therapy data relating to a session of respiratory pressure therapy, therapy summary data for the session, the therapy summary data comprising one or more statistics summarising the therapy data, and compute, from the therapy summary data, a score indicating a probability that the patient will meet a compliance standard, the therapy management server being configured to: update a workflow group of patients depending on the score; and serve a graphical layout representing the workflow group.

Example 71

A method of managing one or more patients undergoing respiratory pressure therapy in one or more servers having one or more processors, the method comprising: communicating with a respiratory pressure therapy device, the respiratory pressure therapy device configured to deliver respiratory pressure therapy to a patient, and generate therapy data relating to a session of respiratory pressure therapy, computing, from the therapy data, therapy summary data for the session, the therapy summary data comprising one or more statistics summarising the therapy data; computing, from the therapy summary data, a score indicating a probability that the patient will meet a compliance standard; updating a workflow group of patients depending on the score; and serving a graphical layout representing the workflow group.

Example 72

A respiratory pressure therapy management server configured to: receive a score indicating a probability that a patient receiving respiratory pressure therapy will meet a compliance standard; update a workflow group of patients depending on the score; and serve a graphical layout representing the workflow group.

Example 73

A system for managing patient compliance with respiratory pressure therapy, the system comprising: one or more processors configured to receive data concerning patient respiratory pressure therapy from a plurality of respiratory pressure therapy devices, the one or more processors further configured to: group patients receiving the respiratory pressure therapy into one or more groups based on a set of rules that evaluate the received data, the rules comprising (a) a compliance risk assessment based on usage data of the received data and (b) a time-based assessment, the time-based assessment comprising a period of days that a patient has been on therapy; and generate a display representing the groups.

Example 74

A system according to Example 73 (or any one of the preceding Examples), wherein the display comprises, for each group, a text heading and a number of patients in the group.

Example 75

A system according to Example 73 (or any one of the preceding Examples), wherein the one or more processors comprise a therapy management server configured to generate, upon activation of a group in the display, a further display identifying the patients in the group.

Example 76

A system according to Example 75 (or any one of the preceding Examples), wherein the further display comprises a checkbox associated with each patient in the group, the checkbox being configured to be checked upon the patient being contacted.

Example 77

The patient management system according to any one of Examples 73-76 (or any one of the preceding Examples), further comprising the plurality of respiratory pressure therapy devices.

Example 78

A method of managing patient compliance with respiratory pressure therapy, the method comprising: receiving, in one or more processors, data concerning patient respiratory pressure therapy from a plurality of respiratory pressure therapy devices, grouping, in the one or more processors, patients receiving the respiratory pressure therapy into one or more groups based on a set of rules that evaluate the received data, the rules comprising (a) a compliance risk assessment based on usage data of the received data and (b) a time-based assessment, the time-based assessment comprising a period of days that a patient has been on therapy; and generating, with the one or more processors, a display representing the groups.

Example 79

The method according to Example 78 (or any one of the preceding Examples), wherein the display comprises, for each group, a text heading and a number of patients in the group.

Example 80

A method according to Example 78 (or any one of the preceding Examples), wherein the one or more processors comprise a therapy management server, and wherein the method further comprises generating, upon activation of a group in the display, a further display identifying the patients in the group with the therapy management server.

Example 81

A method according to Example 80 (or any one of the preceding Examples), wherein the further display comprises a checkbox associated with each patient in the group, the checkbox being configured to be checked upon the patient being contacted.

The invention claimed is:

1. A patient management system comprising:
   a data server, the data server being configured to:
      receive, from a respiratory pressure therapy device in communication with the data server, therapy data relating to a session of respiratory pressure therapy provided to a patient;
      compute, from the therapy data, therapy summary data for the session, the therapy summary data comprising a usage time and a leak flow rate; and
      apply a predictive model to the therapy summary data to compute a score indicating a predictive probability that the patient will meet a compliance standard, the compliance standard having a minimum amount of usage per session for a fraction of a number of consecutive sessions of respiratory pressure therapy; and
   a therapy management server in communication with the data server and a computing device, the therapy management server being configured to:
      obtain a plurality of patient workflow groups, wherein the patient workflow groups comprise a first patient workflow group of patients at risk of not being compliant with the compliance standard;
      update the first patient workflow group to include the patient based on a comparison between the score and a first threshold indicating that the patient should be added to the first patient workflow group;
      serve to the computing device a first graphical layout comprising an array of selectable headings, wherein each of the selectable headings represents one of the obtained patient workflow groups, and wherein the selectable headings comprise a first selectable heading for the first patient workflow group;
      receive a selection of the first selectable heading via an interaction with the first graphical layout;
      in response to receiving the selection of the first selectable heading, serve to the computing device a second graphical layout comprising details of one or more patients in the first patient workflow group, wherein the details of the one or more patients in the first patient workflow group comprise a selectable name for each of the one or more patients;
      receive a selection of any one of the selectable names via an interaction with the second graphical layout;
      in response to receiving the selection of the any one of the selectable names, serve to the computing device a corresponding patient menu comprising one or more selectable options relating to the corresponding patient, wherein one selectable option is a workflow history option;
      receive a selection of the workflow history option; and
      in response to receiving the selection of the workflow history option: obtain a list of patient workflow groups to which the corresponding patient has previously been added; and
      serve to the computing device the list of patient workflow groups to which the corresponding patient has previously been added.

2. The patient management system according to claim 1, wherein each entry of the list comprises the name of a patient workflow group to which the corresponding patient has previously been added, and the date on which the corresponding patient was added to the patient workflow group.

3. The patient management system according to claim 1, wherein the second graphical layout comprises a selectable checkbox positioned by each of the selectable names, and wherein the therapy management server is further configured to:
   receive a selection of any one of the selectable checkboxes; and
   in response to receiving the selection of the any one of the selectable checkboxes, remove the corresponding patient from the first patient workflow group.

4. The patient management system according to claim 1, wherein the score is a numerical probability that the patient will meet the compliance standard.

5. The patient management system according to claim 4, wherein updating the first patient workflow group comprises adding the patient to the first patient workflow group upon the score being less than or equal to the first threshold.

6. The patient management system according to claim 5, wherein the therapy management server is further configured to carry out an action upon the score being less than or equal to the threshold.

7. The patient management system according to claim 6, wherein the action comprises sending a notification to the computing device, and wherein the notification prompts an access to the therapy management server.

8. The patient management system according to claim 6, wherein the action comprises removing the patient from another patient workflow group.

9. The patient management system according to claim 1, wherein the predictive model further takes into account profile data of the patient.

10. The patient management system according to claim 1, wherein the patient is associated with a payor, and wherein the first threshold is specific to the payor.

11. The patient management system according to claim 1, wherein the first threshold is dependent on how long the patient has been receiving respiratory pressure therapy.

12. The patient management system according to claim 1, wherein the one or more patients in the first patient workflow group are ranked within the second graphical layout according to scores obtained from the predictive model.

13. The patient management system according to claim 1, wherein the data server is coincident with the therapy management server.

14. The patient management system according to claim 1, wherein the predictive model applies weighting coefficients to the usage time and the leak flow rate, and wherein the weighting coefficients applied to the usage time and the leak flow rate are selected based on a number of sessions of respiratory pressure therapy provided to the patient.

15. The patient management system according to claim 14, wherein the predictive model is a linear predictive model, a neural network, a decision tree ensemble, a support vector machine, a Bayesian network, or a gradient boosting machine.

16. The patient management system according to claim 1, wherein the obtained patient workflow groups further comprise a second patient workflow group, wherein the selectable headings further comprise a second selectable heading for the second patient workflow group, and wherein the therapy management server is further configured to:
update the second patient workflow group based on whether the usage time currently meets the compliance standard;
receive a selection of the second selectable heading; and
in response to receiving the selection of the second selectable heading, serve to the computing device a third graphical layout comprising details of one or more patients in the second patient workflow group.

17. The patient management system according to claim 16, wherein the obtained patient workflow groups further comprise a third patient workflow group, wherein the selectable headings further comprise a third selectable heading for the third patient workflow group, and wherein the therapy management server is further configured to:
update the third patient workflow group based on a comparison between the leak flow rate and a second threshold;
receive a selection of the third selectable heading; and
in response to receiving the selection of the third selectable heading, serve to the computing device a fourth graphical layout comprising details of one or more patients in the third patient workflow group.

18. The patient management system according to claim 1, wherein the therapy summary data further comprises an Apnea/Hypopnea Index (AHI).

19. The patient management system according to claim 18, wherein the obtained patient workflow groups further comprise a second patient workflow group, wherein the selectable headings further comprise a second selectable heading for the second patient workflow group, and wherein the therapy management server is further configured to:
update the second patient workflow group based on a comparison between the AHI and a second threshold;
receive a selection of the second selectable heading; and
in response to receiving the selection of the second selectable heading, serve to the computing device a third graphical layout comprising details of one or more patients in the second patient workflow group.

20. The patient management system according to claim 1, wherein the array of selectable headings comprises at least three selectable headings, and wherein the selectable headings are arranged within the first graphical layout in columns and rows.

21. The patient management system according to claim 20, wherein each of the selectable headings is a text heading summarizing a rule associated with the corresponding patient workflow group.

22. The patient management system according to claim 20, wherein a number is positioned by each of the selectable headings, and wherein each of the numbers indicates the number of patients in the corresponding patient workflow group.

23. The patient management system according to claim 20, wherein the details of the one or more patients in the first patient workflow group are arranged within the second graphical layout in columns and rows, and wherein one column comprises a selectable name for each of the one or more patients.

24. The patient management system according to claim 23, wherein one column comprises an icon for each of the one or more patients in the first patient workflow group, and wherein each icon indicates whether the corresponding patient meets the compliance standard.

25. The patient management system according to claim 23, wherein one column comprises an icon for each of the one or more patients in the first patient workflow group, wherein each icon indicates whether a property of a session of respiratory pressure therapy provided to the corresponding patient exceeds a second threshold, and wherein the second threshold is a usage time or a leak flow rate.

26. The patient management system according to claim 1, wherein the details of the one or more patients in the first patient workflow group are arranged within the second graphical layout in columns and rows, wherein a first column comprises a selectable name for each of the one or more patients, wherein a second column comprises an icon for each of the one or more patients in the first patient workflow group, and wherein each icon is (a) darkly filled if the corresponding patient meets the compliance standard on a corresponding date, (b) lightly filled if the corresponding patient does not meet the compliance standard on the corresponding date, and (c) unfilled if no data is available for the corresponding patient on the corresponding date.

27. The patient management system according to claim 26, wherein each icon comprises (a) an overbar if an Apnea/Hypopnea Index (AHI) of the corresponding patient on the corresponding date is above a second threshold and (b) an underbar if an average leak flow rate of the corresponding patient on the corresponding date is above a third threshold.

28. The patient management system according to claim 1, wherein the one or more selectable options further comprise a charts option, a contact info option, and a notes option, and wherein the therapy management server is further configured to:
receive a selection of the charts option;
in response to receiving the selection of the charts option, serve to the computing device a third graphical layout comprising a chart illustrating one or more properties of a session of respiratory pressure therapy;
receive a selection of the contact info option;

in response to receiving the selection of the contact info option, serve to the computing device a fourth graphical layout comprising contact details for the corresponding patient;
receive a selection of the notes option; and
in response to receiving the selection of the notes option, serve to the computing device a fifth graphical layout comprising a summary of when the corresponding patient has been contacted by a durable medical equipment provider (DME).

29. A method of managing one or more patients undergoing respiratory pressure therapy, the method comprising:
receiving, with one or more servers having one or more processors, therapy data relating to a session of respiratory pressure therapy provided to a patient from a respiratory pressure therapy device;
computing, with the one or more servers, therapy summary data for the session from the therapy data, the therapy summary data comprising a usage time and a leak flow rate;
applying, with the one or more servers, a predictive model to the therapy summary data to compute a score indicating a predictive probability that the patient will meet a compliance standard, the compliance standard having a minimum amount of usage per session for a fraction of a number of consecutive sessions of respiratory pressure therapy;
obtaining, with the one or more servers, a plurality of patient workflow groups, wherein the patient workflow groups comprise a first patient workflow group of patients at risk of not being compliant with the compliance standard;
updating, with the one or more servers, the first patient workflow group to include the patient based on a comparison between the score and a first threshold indicating that the patient should be added to the first patient workflow group;
serving, with the one or more servers, a first graphical layout to a computing device, the first graphical layout comprising an array of selectable headings, wherein each of the selectable headings represents one of the obtained patient workflow groups, and wherein the selectable headings comprise a first selectable heading for the first patient workflow group;
receiving, with the one or more servers, a selection of the first selectable heading via an interaction with the first graphical layout; and
in response to receiving the selection of the first selectable heading, serving, with the one or more servers, a second graphical layout to the computing device, the second graphical layout comprising details of one or more patients in the first patient workflow group, wherein the details of the one or more patients in the first patient workflow group comprise a selectable name for each of the one or more patients;
receiving, with the one or more servers, a selection of any one of the selectable names via an interaction with the second graphical layout;
in response to receiving the selection of the any one of the selectable names, serving, with the one or more servers, a corresponding patient menu to the computing device, wherein the corresponding patient menu comprises one or more selectable options relating to the corresponding patient, and wherein one selectable option is a workflow history option;
receiving, with the one or more servers, a selection of the workflow history option; and
in response to receiving the selection of the workflow history option: obtaininq, with the one or more servers, a list of patient workflow groups to which the corresponding patient has previously been added; and
serving, with the one or more servers, the list of patient workflow groups to which the corresponding patient has previously been added to the computing device.

30. The method according to claim 29 further comprising:
contacting at least one patient in the first patient workflow group to provide assistance with a respiratory pressure therapy.

* * * * *